(12) United States Patent
Nam et al.

(10) Patent No.: US 11,260,087 B2
(45) Date of Patent: Mar. 1, 2022

(54) **COMPOSITION FOR PREVENTING OR TREATING MENOPAUSE, CONTAINING *LACTOBACILLUS ACIDOPHILUS***

(71) Applicant: KOREA FOOD RESEARCH INSTITUTE, Seongnam-si (KR)

(72) Inventors: Young-Do Nam, Seongnam-si (KR); Yun-Tai Kim, Yongin-si (KR); Hee Soon Shin, Anyang-si (KR); So-Young Lee, Yongin-si (KR); Jae-Goo Kim, Yongin-si (KR); Eun-Yeong Lim, Chungcheongnam-do (KR); Eun-Ji Song, Busan (KR)

(73) Assignee: KOREA FOOD RESEARCH INSTITUTE, Seongnam-si (KR)

( * ) Notice: Subject to any disclaimer, the term of this patent is extended or adjusted under 35 U.S.C. 154(b) by 34 days.

(21) Appl. No.: 16/325,018

(22) PCT Filed: Aug. 11, 2017

(86) PCT No.: PCT/KR2017/008737
§ 371 (c)(1),
(2) Date: Feb. 12, 2019

(87) PCT Pub. No.: WO2018/030837
PCT Pub. Date: Feb. 15, 2018

(65) Prior Publication Data
US 2019/0192591 A1     Jun. 27, 2019

(30) Foreign Application Priority Data

Aug. 12, 2016  (KR) .................. 10-2016-0103280
Aug. 10, 2017  (KR) .................. 10-2017-0101649

(51) Int. Cl.
| A61K 35/747 | (2015.01) |
| C12N 1/20 | (2006.01) |
| A23L 33/135 | (2016.01) |
| A61Q 19/08 | (2006.01) |
| A61P 15/00 | (2006.01) |
| A61K 8/99 | (2017.01) |
| A61Q 19/00 | (2006.01) |
| C12R 1/23 | (2006.01) |

(52) U.S. Cl.
CPC .......... *A61K 35/747* (2013.01); *A23L 33/135* (2016.08); *A61K 8/99* (2013.01); *A61P 15/00* (2018.01); *A61Q 19/00* (2013.01); *A61Q 19/08* (2013.01); *C12N 1/20* (2013.01); *C12N 1/205* (2021.05); *A23V 2002/00* (2013.01); *A23Y 2220/03* (2013.01); *C12R 2001/23* (2021.05)

(58) Field of Classification Search
CPC ........ A61K 35/747; A61K 8/99; A61Q 19/08; A61Q 19/00; A61P 15/00; A61P 15/12; C12R 1/23; C12N 1/20; A23L 33/135; A23V 2002/00; A23V 2200/302; A23Y 2220/03
See application file for complete search history.

(56) References Cited

U.S. PATENT DOCUMENTS

| 2009/0104167 A1* | 4/2009 | Hattori | A61K 35/747 424/93.45 |
| 2015/0230485 A1* | 8/2015 | Ohmachi | A23C 9/1465 424/94.6 |
| 2015/0313949 A1* | 11/2015 | Cutillo | A61K 35/22 424/563 |
| 2016/0192689 A1* | 7/2016 | Horn | A23L 33/22 424/439 |
| 2017/0347689 A1* | 12/2017 | Wu | A23L 2/52 |

FOREIGN PATENT DOCUMENTS

| JP | 2012-527413 A | 11/2012 |
| KR | 10-2009-0088205 A | 8/2009 |
| KR | 10-2012-0001283 A | 1/2012 |
| KR | 10-1279852 B1 | 7/2013 |
| KR | 10-2015-0106478 A | 9/2015 |
| KR | 10-2015-0123207 A | 11/2015 |
| KR | 10-2015-0133284 A | 11/2015 |
| WO | 2007/013547 A1 | 2/2007 |
| WO | 2010/133314 A1 | 11/2010 |

OTHER PUBLICATIONS

Donders, G. et al., Ultra-low-dose estriol and Lactobacillus acidophilus vaginal tablets (Gynoflor) for vaginal atrophy in postmenopausal breast cancer patients on aromatase inhibitors: pharmacokinetic, safety, and efficacy phase I clinical study, Breast Caner Res Treat, 145(2), 371-379 (Year: 2014).*
Davis, S.R. et al., Understanding weight gain at menopause, 2012, Climacteric, 15:5, 419-429 (Year: 2012).*
Hopkins Medicine, https://www.hopkinsmedicine.org/health/conditions-and-diseases/osteoporosis/osteoporosis-what-you-need-to-know-as-you-age, Apr. 17, 2020 (Year: 2020).*
Donders et al., Ultra-low-dose estriol and Lactobacillus cidophilus vaginal tablets (Gynoflor(R)) for vaginal atrophy in postmenopausal breast cancer patients on aromatase inhibitors: pharmacokinetic, safety, and efficacy phase I clinical study, Breast Cancer Research and Treatment, Apr. 10, 2014, vol. 145(2), pp. 371-379.
Lim et al., "Physiological Characteristics and GABA Production of Lactobacillus acidophilus RMK567 Isolated from Raw Milk", Korean J. Food Sci. Ani. Resour., 2009, vol. 29(1), pp. 15-23.

* cited by examiner

*Primary Examiner* — Olivia M. Wise
*Assistant Examiner* — Anjali Ajit Hirani
(74) *Attorney, Agent, or Firm* — Vorys, Sater, Seymour and Pease LLP; Mih Suhn Koh

(57) ABSTRACT

Provided is a novel *Lactobacillus acidophilus* YTI strain (deposition number: KCCM 11808P); and a composition for preventing, alleviating, or treating menopause, comprising, as an active ingredient, *Lactobacillus acidophilus* comprising the novel strain.

1 Claim, 23 Drawing Sheets
Specification includes a Sequence Listing.

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: 9F_universal primer

<400> SEQUENCE: 1
gagtttgatc atggctcag                                                19

<210> SEQ ID NO 2
<211> LENGTH: 19
<212> TYPE: DNA
<213> ORGANISM: Artificial Sequence
<220> FEATURE:
<223> OTHER INFORMATION: 356R_universal primer

<400> SEQUENCE: 2
tgctgcctcc cgtaggagt                                                19
```

COMPOSITION FOR PREVENTING OR TREATING MENOPAUSE, CONTAINING *LACTOBACILLUS ACIDOPHILUS*

CROSS-REFERENCE TO RELATED APPLICATION

This application is a 371 of PCT/KR2017/008737, filed Aug. 11, 2017, which claims the benefit of priority from Korean Patent Application No. 10-2016-0103280, filed Aug. 12, 2016 and Korean Patent Application No. 10-2017-0101649, filed Aug. 10, 2017, the contents of each of which are incorporated herein by reference in its entirety.

STATEMENT REGARDING GOVERNMENT RIGHTS

The present invention was undertaken with the support of 1) Development of Nutraceutical and Pharmaceutical Materials for Pain Relief No. E0164502-03 grant funded by the Ministry of Science and ICT, and 2) Development of Healthcare Platform based on Gut Microbial Information No. E0170602-02 grant funded by the Ministry of Science and ICT.

SEQUENCE LISTING

The Sequence Listing submitted in text format (.txt) filed on Feb. 12, 2019, named "SequenceListing.txt", created on Feb. 11, 2019 (760 bytes), is incorporated herein by reference.

TECHNICAL FIELD

The present invention relates to a novel *Lactobacillus acidophilus* YT1 strain (Deposition Number: KCCM11808P), and a composition for preventing, alleviating or treating menopause, which includes *Lactobacillus acidophilus* including the novel strain as an active ingredient.

BACKGROUND ART

Intestinal microorganisms in the body can be classified by individuals, and these microorganisms are known to be involved in various metabolisms in the intestinal tract. Particularly, intestinal microorganisms related to obesity are a well-known area, and obese persons have been reported to abundantly have intestinal microorganisms related to metabolism of carbohydrates, fats and amino acids. In addition, materials such as butyrates or acetates, produced by the metabolism of intestinal microorganisms are a critical factor of gastrointestinal immunity, and have been reported to protect a living organism from pathogenic infection through regulation of the production of helper T cells or the reaction with G-protein receptor 43 (GPR43). In addition, intestinal microorganisms have been identified as causes of autism, atopy, etc., as well as various diseases in the large intestine such as inflammatory bowel disease or colon cancer. It has been reported that, through the communication between the intestinal microorganisms and the central nervous system, the regulation of serotonin production in enterochromaffin cells present in the intestinal duct by intestinal microorganisms affects the mood of the organisms, and the intestinal microorganisms can be modulated through an indirect method such as modulation of the nervous system or intestinal movement, or modulation of intestinal permeability and a direct method such as the secretion of signaling substances from hormone-secreting cells present in the intestinal duct, the nervous system or immune cells. This means that the change in intestinal microorganisms can control the emotions of the living organisms.

Recently, there has been research on the human body to investigate the correlation between hormone levels and intestinal microorganisms in premenopausal and postmenopausal women. However, the research only identified a decrease in the overall number of microorganisms, rather than finding the specific change in microorganisms. However, the research revealed that the hormonal change leads to a significant change in intestinal microorganisms (Jour. Transl. Med. 2012; 10: 253).

Many studies have shown that menopausal symptoms can be prevented by a proper diet, and particularly, according to the WHO, it has been known that one third of the typical menopausal symptoms can be prevented by the intake of foods such as vegetables and fruits, and to this end, the intake of foods derived from natural products is recommended, rather than synthetic hormone replacement therapy (HRT). While some study results have shown that isoflavone used as a synthetic hormone substitute is effective for reduction of menopausal symptoms, there is a lack of evidence in that natural product-derived food is more effective than a synthetic hormone substitute, and it has been reported that excessive intake results in endometrial hyperplasia and the proliferation of breast epithelial cells. Therefore, through profound research, it is necessary to develop technology which can satisfy criteria for a novel natural product-derived hormone substitute.

It has been known that a high estrogen level in the body raises the incidence of breast cancer, and a low estrogen level raises the incidence of osteoporosis. For this reason, it is considered that it is important to regulate estrogen to a suitable level in the body. A recent study showed that intestinal microorganisms affect the regulation of estrogen in the body through enterohepatic circulation, which is interpreted as a result of maintaining estrogen homeostasis in the body by reuse after conjugated estrogen introduced into the intestine is metabolized and soluble estrogen is converted to compensate for an estrogen deficiency in the body as a result of the interaction between the body and intestinal microorganisms. It is necessary to clearly demonstrate whether postmenopausal symptoms such as osteoporosis, cognitive decline and depression are influenced by estrogen itself or by intestinal microorganisms by confirming how the estrogen reduction in menopause affects intestinal microorganisms or how the change of key microorganisms affects the body, and it is necessary to identify the change in intestinal microorganisms caused by menopause and to clarify how the change in key microorganisms affects the health of a host.

DISCLOSURE

Technical Problem

The inventors have established a menopausal animal model through ovariectomy to analyze the change in intestinal microorganisms, and intensively studied to develop a microbial material for improving menopause symptoms, such that a novel *Lactobacillus acidophilus* YT1 strain (Deposition Number: KCCM11808P) was identified and isolated from intestinal microorganisms which are significantly changed in distribution in the menopausal animal model compared with a control, and a menopausal symptom-improving effect of a *Lactobacillus acidophilus* strain including the novel strain was confirmed. Therefore, the present invention was completed.

The present invention is directed to providing a *Lactobacillus acidophilus* YT1 strain (Deposition Number: KCCM11808P) which is effective in preventing or treating menopause.

The present invention is also directed to providing a composition for preventing, alleviating or treating menopause, which includes *Lactobacillus acidophilus* including the novel strain as an active ingredient.

However, technical problems to be solved in the present invention are not limited to the above-described problems, and other problems which are not described herein will be fully understood by those of ordinary skill in the art from the following descriptions.

Technical Solution

One aspect of the present invention provides a novel *Lactobacillus acidophilus* YT1 strain (Deposition Number: KCCM11808P) which is effective in preventing or treating menopause.

Another aspect of the present invention provides a pharmaceutical composition for preventing or treating menopause, a food composition for alleviating menopause, and/or a cosmetic composition for alleviating menopause, which include *Lactobacillus acidophilus* including the novel strain as an active ingredient.

Still another aspect of the present invention provides a pharmaceutical composition for preventing or treating menopause, a food composition for alleviating menopause, and/or a cosmetic composition for alleviating menopause, which include *Lactobacillus acidophilus* as an active ingredient.

According to an exemplary embodiment of the present invention, the food composition may include a health functional food composition.

According to another exemplary embodiment of the present invention, the *Lactobacillus acidophilus* may be a *Lactobacillus acidophilus* YT1 strain or a *Lactobacillus acidophilus* KCTC 3164 strain.

According to still another exemplary embodiment of the present invention, the composition may inhibit an increase in body fat due to menopause.

According to yet another exemplary embodiment of the present invention, the composition may inhibit a decrease in bone mineral density due to menopause.

According to yet another exemplary embodiment of the present invention, the composition may inhibit an increase in pain sensitivity due to menopause.

According to yet another exemplary embodiment of the present invention, the composition may alleviate depression due to menopause.

Yet another aspect of the present invention provides a method for preventing or treating menopause, which includes administering a pharmaceutical composition including *Lactobacillus acidophilus* as an active ingredient to a subject.

Yet another aspect of the present invention provides a use of *Lactobacillus acidophilus* for preventing or treating menopause.

Advantageous Effects

The inventors have established a menopausal animal model through ovariectomy, confirmed changes in the distribution of intestinal microorganisms therefrom, identified and isolated a novel *Lactobacillus acidophilus* strain among lactic acid bacteria which is significantly reduced in distribution in the menopausal model, and confirmed effects of the novel strain and the previously reported *Lactobacillus acidophilus* strains on alleviating menopausal symptoms, such as the inhibition of an increase in body fat, the inhibition of a decrease in bone mineral density, the inhibition of an increase in pain sensitivity, and the alleviation of depression. Therefore, it is expected that the composition containing the *Lactobacillus acidophilus* according to the present invention can be effectively used for preventing, alleviating or treating menopause.

DESCRIPTION OF DRAWINGS

FIGS. 5A and 5B show analysis results of cytokine concentrations in the immune system in a control (Sham) and an ovariectomy group (OVX) at week 18 after female rats were subjected to ovariectomy, in which FIG. 5A is a result of measuring various concentrations of cytokines (IL-1$\alpha$, 1$\beta$, 2, 4, 6, 10, 12, 13, INF-$\gamma$, TNF-$\alpha$, GM, and RANTES) in a Peyer's patch, and FIG. 5B is a result of measuring IL-10 concentrations in a Peyer's patch and the spleen.

MODES OF THE INVENTION

Figure 1:
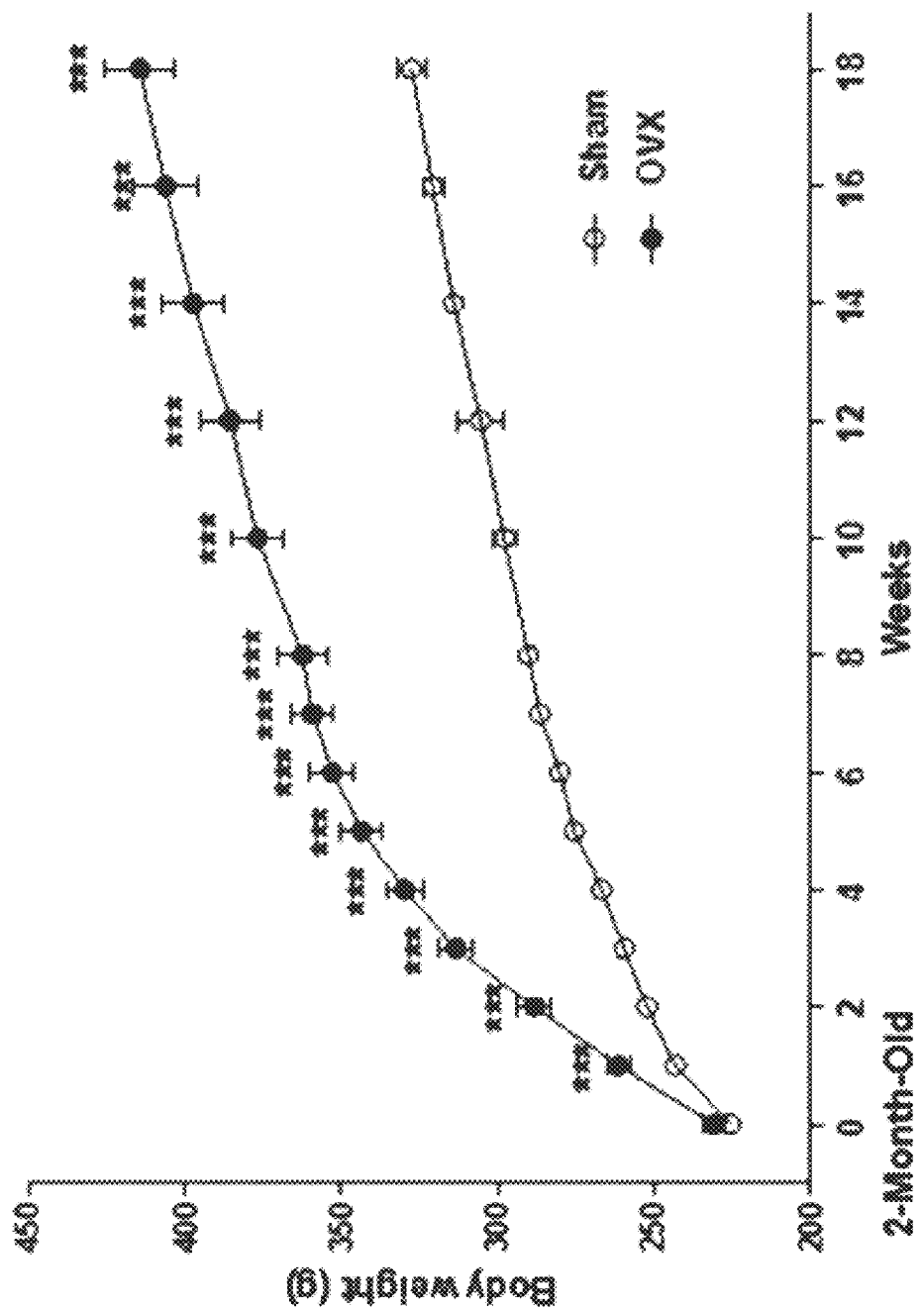
FIG. 1 shows a result of comparing a body weight between a control (Sham) and an ovariectomy group (OVX), measured at intervals of two weeks for 18 weeks after female rats were subjected to ovariectomy.

The present invention relates to a novel *Lactobacillus acidophilus* strain isolated from the feces of a menopause rat model and a composition for preventing, alleviating or treating menopause, which includes *Lactobacillus acidophilus* containing the strain as an active ingredient.

The inventors had analyzed the change in intestinal microorganisms due to menopause by establishing a menopausal animal model through ovariectomy, and studied to develop a microbial material for alleviating menopausal symptoms, such that a *Lactobacillus acidophilus* strain which was significantly reduced in distribution was identified and isolated from a menopausal animal model, and an effect of alleviating menopausal symptoms by *Lactobacillus acidophilus* including the strain was confirmed, and therefore, the present invention was completed.

Accordingly, the present invention provides a *Lactobacillus acidophilus* YT1 strain (Deposition Number: KCCM11808P) which is effective in preventing or treating menopause.

The inventors named the novel strain *Lactobacillus acidophilus* YT1, which was deposited in the Korea Culture Center of Microorganisms (KCCM) on Jan. 20, 2016 under Deposition Number KCCM11808P.

In addition, the present invention provides a pharmaceutical composition for preventing or treating menopause, which includes *Lactobacillus acidophilus* including the novel strain as an active ingredient.

The term "prevention" used herein refers to all actions of inhibiting menopausal symptoms or delaying the onset thereof by administration of the pharmaceutical composition according to the present invention.

The term "treatment" used herein refers to all actions involved in alleviating or beneficially changing menopausal symptoms by administration of the pharmaceutical composition according to the present invention.

In the present invention, the *Lactobacillus acidophilus* effective in preventing or treating menopause includes a conventionally known *Lactobacillus acidophilus* strain, as well as a novel strain (YT1) isolated and identified from the feces of a menopausal rat model of the present invention, and in the present invention, the effect of *Lactobacillus acidophilus* on prevention or treatment of menopause was first identified.

The climacteric, which is a target disease of the present invention, is also referred to as menopause, which means the time when menstruation stops permanently as the sign of the loss of a woman's reproductive function. In menopause, due to the loss of an ovarian function, the amount or period of menstruation becomes irregular, a decrease in secretion of follicular hormone (estrogen) over several months to three years results in termination of menstruation, and acts on the autonomic nerve center of the diencephalon, thereby causing autonomic dysfunction and a menopausal disorder. In addition, a masculinizing effect is caused by the hyperfunction of the adrenocortical function due to the dysfunction of the anterior pituitary gland, and menopause-specific dysfunction such as obesity caused by thyroid dysfunction due to the effect of a thyroid hormone. For example, symptoms such as hot flashes, palpitations, dizziness, tinnitus, hypertension, a digestive disorder, headaches, hypomnesia, depression, etc. may occur.

In the present invention, a menopausal model is manufactured by removing the ovaries from a female rat, and compared with a normal control to analyze the change in intestinal microorganisms, thereby identifying and isolating a *Lactobacillus acidophilus* novel strain which is significantly reduced in distribution from a menopause model, and confirming an effect of alleviating menopausal symptoms caused by administration of *Lactobacillus acidophilus*.

In an exemplary embodiment of the present invention, a menopause model from which the ovaries are removed is manufactured, and compared with a normal control, subsequently, it is confirmed that a menopause model is well established by measuring a body weight, a bone mineral density, an organ weight, a length change, a blood biochemical index, blood estradiol, and a cytokine concentration in the immune system (see Example 2).

In another exemplary embodiment of the present invention, the change in distribution of intestinal microorganisms is confirmed through metagenomic analysis by comparing the established menopausal animal model with the normal control, and finally, 10 species of microorganisms which are reduced in distribution in a menopause model are identified from 32 species of intestinal microorganisms which have been finally found (see Example 3).

In still another exemplary embodiment of the present invention, based on the result of Example 3, *Lactobacillus acidophilus* showing the biggest difference among lactic acid bacteria significantly reduced in distribution in the menopause models which have been subjected to ovariectomy is selected and the strain is isolated from a fecal sample (see Example 4).

In yet another exemplary embodiment of the present invention, the novel *Lactobacillus acidophilus* strain (YT1) isolated in the present invention and a known *Lactobacillus acidophilus* strain (KCTC 3164) are orally administered to menopause models, respectively, and a body weight, a body fat mass, the change in eating behavior, a femoral bone mineral density, pain sensitivity, and depression-like behavior are analyzed, confirming that menopausal symptoms are alleviated by the administration of the strains (see Example 5).

In accordance with the list of prokaryotic names with standing in nomenclature (LPSN) and Korean Collection for Type Collection (KCTC), the *Lactobacillus acidophilus* strain (KCTC 3164) is a representative strain among *Lactobacillus acidophilus* strains.

In yet another exemplary embodiment of the present invention, the novel *Lactobacillus acidophilus* strain (YT1) isolated in the present invention and the strain of a different species of the genus *Lactobacillus* (*Lactobacillus reuteri* (*L. reuteri*)) are orally administered into menopause models, respectively, and a femoral bone mineral density and pain sensitivity are analyzed, confirming that menopausal symptoms are alleviated by the administration of the *Lactobacillus acidophilus* strain (YT1) (see Example 6).

In view of the above results, the *Lactobacillus acidophilus* strain according to the present invention may be effectively used in prevention, alleviation or treatment of menopause.

The pharmaceutical composition according to the present invention includes *Lactobacillus acidophilus* as an active ingredient, and further includes a pharmaceutically acceptable carrier. The pharmaceutically acceptable carrier is commonly used in formulation, and may be saline, sterile water, Ringer's solution, buffered saline, cyclodextrin, a dextrose solution, a maltodextrin solution, glycerol, ethanol, or a liposome, but the present invention is not limited thereto. The pharmaceutical composition according to the present invention may further include other common additives such as an antioxidant, a buffer, etc., if needed. In addition, by additionally adding a diluent, a dispersant, a surfactant, a binder, a lubricant, etc., the pharmaceutical composition according to the present invention may be formulated as an injectable form such as an aqueous solution, a suspension or an emulsion, a pill, a capsule, a granule or a tablet. Suitable pharmaceutically acceptable carriers and their formulations may be prepared according to each ingredient using a method disclosed in the Remington's Pharmaceutical Science. The pharmaceutical composition of the present invention is not limited in dosage form, and thus may be prepared as injections, inhalants, external preparations for skin, etc.

The pharmaceutical composition of the present invention may be administered orally or non-orally (e.g., intravenously, subcutaneously, intraperitoneally, or local) according to a desired method, and a dose of the pharmaceutical composition of the present invention may be selected according to a patient's condition and a body weight, severity of a disease, a dosage form, an administration route and duration by those of ordinary skill in the art.

The composition of the present invention is administered at a pharmaceutically effective amount. In the present invention, the "pharmaceutically effective amount" refers to an amount sufficient to treat the disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field. The composition of the present invention may be administered separately or in combination with other therapeutic agents, and may be sequentially or simultaneously administered with a conventional therapeutic agent, or administered in a single dose or multiple doses. In consideration of all of the above-mentioned parameters, it is important to achieve the maximum effect with the minimum dose without a side effect, and such a dose may be easily determined by one of ordinary skill in the art.

Specifically, the effective amount of the pharmaceutical composition according to the present invention may vary depending on a patient's age, sex, condition, a body weight, an absorption degree of an active ingredient in the body, inactivity and an excretion rate, the type of a disease, and a drug used in combination, and may be generally administered at 0.001 to 150 mg, and preferably, 0.01 to 100 mg/kg of body weight daily or every other day, or one to three times a day. However, the effective amount may vary depending on an administration route, the severity of obesity, sex, a body weight or age, and therefore the scope of the present invention is not limited by the dose in any way.

As another aspect of the present invention, the present invention provides a food composition for alleviating menopause, which includes *Lactobacillus acidophilus* including the novel strain as an active ingredient.

In the present invention, the food composition may include a health functional food composition, but the present invention is not limited thereto.

The term "improvement" used herein refers to all types of actions that at least reduce parameters related to a condition to be treated, for example, a degree of a symptom. Here, the health functional food composition may be used simultaneously or separately with a drug for treatment before or after the onset of a corresponding disease to improve menopause.

The term "health functional food composition" used herein is formulated as one selected from the group consisting of a tablet, a pill, a powder, a granule, a capsule and a liquid by adding one or more of a carrier, a diluent, an excipient and an additive. Foods that can be added to the composition of the present invention may include various foods, powders, granules, tablets, capsules, syrups, beverages, gums, teas, vitamin complexes, and health functional foods. As an additive further included in the present invention, one or more types of ingredients selected from the group consisting of a natural carbohydrate, a sweetener, a nutrient, a vitamin, a mineral (electrolyte), a flavoring agent (synthetic flavoring agent, natural flavoring agent, etc.), a coloring agent, a filler, pectic acid and a salt thereof, alginic acid and a salt thereof, an organic acid, a protective colloid thickening agent, a pH modifier, a stabilizer, a preservative, an antioxidant, glycerin, an alcohol, a carbonating agent, and fruit flesh may be used. Examples of the above-mentioned natural carbohydrates include conventional sugars, for example, monosaccharides such as glucose, fructose, etc.; disaccharides such as maltose, sucrose, etc.; and polysaccharides such as dextrin, cyclodextrin, etc., and sugar alcohols such as xylitol, sorbitol, erythritol, etc. As the sweeteners, natural sweeteners [thaumatin, stevia extract (e.g., rebaudioside A, glycyrrhizin, etc.)] and synthetic sweeteners (saccharin, aspartame, etc.) may be advantageously used. In addition to the above ingredients, the composition according to the present invention may contain a variety of nutrients, vitamins, minerals (electrolytes), flavoring agents including synthetic and natural flavoring agents, coloring agents and fillers (cheese, chocolate, etc.), pectic acid and a salt thereof, alginic acid and a salt thereof, an organic acid, protective colloid thickening agents, pH modifiers, stabilizers, preservatives, glycerin, alcohols, or carbonating agents used in carbonated beverages. In addition, the composition according to the present invention may contain flesh for preparing natural fruit juices and vegetable juices. Such an ingredient may be used independently or in combination. Specific examples of the carriers, excipients, diluents and additives may include, but are not limited to, one or more selected from the group consisting of lactose, dextrose, sucrose, sorbitol, mannitol, erythritol, starch, acacia gum, calcium phosphate, alginate, gelatin, calcium phosphate, calcium silicate, microcrystalline cellulose, polyvinylpyrrolidone, cellulose, methyl cellulose, water, sugar syrup, methyl hydroxybenzoate, propyl hydroxybenzoate, talc, magnesium stearate, and mineral oil.

As still another aspect of the present invention, the present invention provides a cosmetic composition for alleviating menopause, which includes *Lactobacillus acidophilus* including the novel strain as an active ingredient.

The cosmetic composition of the present invention may include ingredients commonly used in a cosmetic composition, as well as *Lactobacillus acidophilus*, and for example, a common additives and carriers such as an antioxidant, a stabilizer, a solubilizer, a vitamin and a flavor.

In addition, the composition of the present invention may be used by being mixed with a conventionally used organic UV blocking agent, which then reacts with *Lactobacillus acidophilus*, in addition to *Lactobacillus acidophilus*, as long as it does not impair a skin protection effect. As the organic UV blocking agent, one or more selected from the group consisting of glyceryl PABA, drometrizole trisiloxane, drometrizole, digalloyl trioleate, disodium phenyl dibenzimidazole tetrasulfonate, diethylhexyl butamido triazone, diethyl amino hydroxybenzoyl hexyl benzoate, DEA-methoxycinnamate, a mixture of lawsone and dihydroxyacetone, methylenebis-benzotriazolyl tetramethylbutylphenol, 4-methylbenzylidene camphor, menthyl anthranilate, benzophenone-3(oxybenzone), benzophenone-4, benzophenone-8 (dioxybenzone), butyl methoxydibenzoylmethane, bisethylhexyloxyphenolmethoxy phenyltriazine, cinoxate, ethyl dihydroxypropyl PABA, octocrylene, ethylhexyl dimethyl PABA, ethylhexyl methoxy cinnamate, ethylhexyl salicylate, ethylhexyltriazone, isoamyl-p-methoxycinnamate, polysilicone-15 (dimethicodiethyl benzal malonate), terephthalylidene dicamphor sulfonic acid and a salt thereof, TEA-salicylate, and aminobenzoic acid (PABA) may be used.

As a product to which the cosmetic composition of the present invention can be added, for example, cosmetics such as an astringent toner, a softening toner, a nourishing toner, various types of creams, essences, packs and foundations, and a cleanser, soap, a treatment or a cosmetic solution may be used. Specific examples of the cosmetic composition of the present invention include a skin lotion, a skin softener, a skin toner, an astringent, a lotion, a milk lotion, a moisturizer lotion, a nourishing lotion, a massage cream, a nourishing cream, a moisturizer cream, a hand cream, an essence, a nourishing essence, a pack, soap, a shampoo, a cleansing foam, a cleansing lotion, a cleansing cream, a body lotion, a body cleanser, an emulsion, a lipstick, a makeup base, a foundation, a pressed powder, a loose powder, and an eyeshadow.

According to an exemplary embodiment of the present invention, a content of *Lactobacillus acidophilus* of the present invention may be 0.00001 to 30 wt %, preferably 0.5 to 20 wt %, and more preferably 1.0 to 10 wt % with respect to a total weight of the composition. When the content of *Lactobacillus acidophilus* is less than 0.00001 wt %, a UV absorbing effect is greatly reduced, and when the content is more than 30 wt %, skin irritation may occur, and there may be a problem in dosage form.

Hereinafter, to help in understanding the present invention, exemplary examples will be suggested. However, the following examples are merely provided to more easily understand the present invention, and not to limit the present invention.

EXAMPLES

Example 1. Experimental Methods and Preparation 1-1. Preparation of Experimental Animals and Menopausal Animal Models To prepare a menopausal animal model, Sprague-Dawley (SD) rats (4-week-old, 100-120 g, female) were bought from Samtako Inc. and acclimated in a breeding cage for 4 weeks for experiments. The acclimation was performed at a temperature of 22±1° C. with 55±5% humidity under a light/dark cycle (12-hr light/12-hr night) at a luminance of 300 Lux, and feed and water were freely provided. In addition, all animals were cared in accordance with the Guidelines for Institutional Animal Care and Use Committee of the Korean Food Research Institute (KFRI-IACUC).

For preparation of menopausal animal models, ovariectomy models were used. To this end, the body weights of animals determined to be normal after the acclimation of the rats were measured, and then the animals were randomly divided into experimental groups. For long-term breeding, each experimental animal was identified by an indicate method with an animal marker and ear tagging. In the experiments, SD female rats (8-week-old, 200-250 g) at a mature phase were used, and the number of individuals was set to be at least 10 (n=10) per group.

For ovariectomy, after shaving and incising the abdomen 1 cm apart from the last right and left ribs, adipose tissue surrounding the ovaries was pulled away to reveal the uterus and remove the ovaries, and then the uterus was replaced in situ. The surgical site was gently compressed to stop the bleeding, and the skin was sutured with nylon 4-0 suture and then irrigated with a 10% povidone-iodine solution. After the surgery, antibiotic ointment was applied to prevent infection, and then the rat was transferred to a breeding cage for recovery. For 24 hours after the operation, the condition of the experimental animal was observed to check for abnormalities.

1-2. Measurement of Body Weight and Fecal Sampling

After ovariectomy was performed on the rats according to the method described in Example 1-1, body weight changes were measured and fecal sampling was performed every week for 10 weeks. From 12 weeks after the surgery to the end of the experiment (18 weeks after the surgery), body weights were measured and fecal samples were collected once every second week. Subsequently, analysis was conducted.

1-3. Measurement of Bone Mineral Density

For long-term observation of body weight change and measurement of bone mineral density after the ovariectomy, a femoral bone mineral density of the experimental animals was measured and analyzed using a bone densitometer (pDEXATM, Norland) by time. The measured area (Area), BMC and BMD of the femoral region were measured using X-rays utilized by the bone densitometer (pDEXATM, Norland), thereby comparatively analyzing the effect of OVX on the change in bone mineral density, and the effect of treatment with candidate intestinal microorganisms on the change in bone mineral density.

1-4. Von Frey Filament Test

To measure a degree of mechanical allodynia of experimental animals after the long-term observation of body weight change and fecal sampling after the ovariectomy, a von Frey filament test was performed 4, 12, 16 and 18 weeks after the surgery. The experimental animals were placed in an acrylic cage equipped with a wire mesh bench and acclimated for 15 minutes or more, and then when the movement of the experimental animals stopped, the mechanical withdrawal threshold (g) was evaluated using von Frey filaments with sequentially-increasing diameters (Stoelting, Inc., USA). The filament was held in vertical contact with a sole of the left lesioned part and maintained for 5 or 6 seconds, and then if the experimental animal showed a rapid avoidance response or immediately flinched or licked the sole while the filament was detached, it was considered a positive response. If a positive response was shown by stimulation of the experimental animal with a von Frey filament with an intermediate diameter, stimulation was performed with a thinner filament, and if there was no positive response, stimulation was performed with a thicker filament. The minimum stimulation level at which a positive response occurs was designated as the threshold, and the filaments were no longer applied at the upper limit set when there was no response even at 15 g or more.

1-5. Forced Swim Test (FST)

Experimental animals were subjected to a forced swim test (FST) 18 weeks after ovariectomy. To this end, a transparent acrylic cylindrical water tank with a height of 50 cm and a diameter of 25 cm was filled with water (23 to 25° C.) to a height at which the tail of a rat did not touch the bottom thereof, and the rat was put into the tank to be forced to swim for 15 minutes. After 24 hours, forced swimming was performed in the same environment for 6 minutes and recorded to perform comparative analysis of time for climbing, swimming, and immobility using the Smart 3.0 program. Here, the climbing is the most intensive exercise as it refers to a state of actively using forepaws to climb the acrylic cylinder with the four limbs, the swimming is the state of moving around on the water surface or occasionally diving under the water, and the immobility is a state in which only a part of the upper body including the head is exposed above the water surface without movement, indicating a rapid depression state due to abandonment of survival. By measuring the time to reach each state, the behavioral changes before and after ovariectomy were comparatively analyzed by FST.

1-6. Metagenomic Analysis for Intestinal Microorganisms

For metagenomic analysis for intestinal microorganisms of menopausal animal models, first, 0.5 g of a rat fecal sample in the Sham group or the ovariectomy (OVX) group was collected, and a metagenome was extracted therefrom. More specifically, 0.5 g of the sample was homogenized with LN2, STES buffer was added thereto, and the sample was cultured at 60° C. overnight, and then the cells were lysed. After cell lysis, a metagenome was extracted from the cell lysate using a phenol extraction (phenol-chloroform-isoamylalcohol (PCI)) method. Afterward, to remove RNA present in the crude metagenome, the resulting product was treated with 10 μL (100 mg/mL) of RNase and incubated for 1 hour, followed by additionally obtaining a metagenome purified having a purity suitable for being used in sequencing using a DNA purification column.

Purification of the obtained metagenome was performed by G-spin Genomic DNA purification, and qualitative/quantitative analyses for DNA were performed. The corresponding genes of the extracted/purified DNA were amplified using universal primers (9F, 5'-GAGTTTGATCATGGCTCAG-3' (SEQ ID NO: 1); 356R, 5'-TGCTGCCTCCCGTAGGAGT-3' (SEQ ID NO: 2)) targeting the ribosomal DNA of bacteria, and a barcode sequence with 8 bases, specific to each sample, was added to the 5' end of the universal primer to allow the sequence derived from each sample to be divided in a subsequent analysis. Afterward, a mixture was prepared by pooling 100 ng of the 16S rDNA amplification product, additionally purified, and then repaired to allow the terminal end to be a blunt end, and specific 50mer oligo adaptors were linked to the 5' and 3' ends of each pooled amplicon using an ion-torrent sequencing adaptor. After adaptor ligation, to collect an adapter ligated fragment with a sequencing target length of 400 bp, size selection was performed using a 2% ethidium free gel manufactured by Pippin Prep, and a total amount of the product was amplified through 5-cycle amplification using a primer binding site at both ends of the adaptor sequence. To confirm the final product, the product was qualitatively/quantitatively analyzed using a bioanalyzer high sensitivity DNA chip by step, and amplicon sequencing was performed using Ion torrent PGM.

Only valid sequences were obtained through a process of aligning sequences derived from respective samples by a Mothur program using the amplicon sequence of the obtained animal model, removing a sequence that did not match a barcode sequence or primer sequence, and removing a sequence read having an N base (ambiguous) in the analyzed sequence. By computing the valid sequence reads, multiple alignment of each sequence was performed to finally acquire only base sequences having the same comparison sequence lengths. Since it is impossible to make an absolute comparison due to a different number of the sequence reads of each sample, random subsampling was performed by random shuffling for the sequence reads obtained from the samples to be used in the final analysis for 1000 sequence reads per sample. Subsequently, sequences derived from each sample were mapped in the reference database to identify the closest microorganisms, and the data was subjected to statistical analysis based on the data using the STAMP program. Through the statistical analysis, the distribution pattern of microorganisms in each period was confirmed by PCA analysis, and the change in major microorganisms and microbial species having significant differences in the final analysis were obtained.

1-7. Statistical Analysis

The experimental results were expressed as mean±SEM, and a significant difference between two groups was evaluated by the Student's t-test. $p<0.05$ was considered statistically significant, and expressed as $p<0.05$ (*), $p<0.01$ () and $p<0.001$ (*). Statistical comparison between experimental groups and the control was performed by one-way ANOVA using the Statview (ver. 5.01, The SAS Institute, CA) program.

Example 2. Analysis of Menopausal Animal Model Through Ovariectomy 2-1. Measurement of Change in Body Weight and Bone Mineral Density A body weight was measured for female rats which had been subjected to ovariectomy according to Example 1-1 for 18 weeks from one week after the surgery by the method described in Example 1-2.

As a result, as shown in FIG. 1, compared with rats in the control (Sham), the OVX group subjected to ovariectomy was significantly increased in body weight continuously from one week after the surgery (***$p<0.001$). The result shows that a menopausal animal model was well established by ovariectomy.

In addition, a bone mineral density of the control (Sham) and the ovariectomy group (OVX) was measured according to the method described in Example 1-3 as another indicator of a menopausal animal model.

Figure 2:
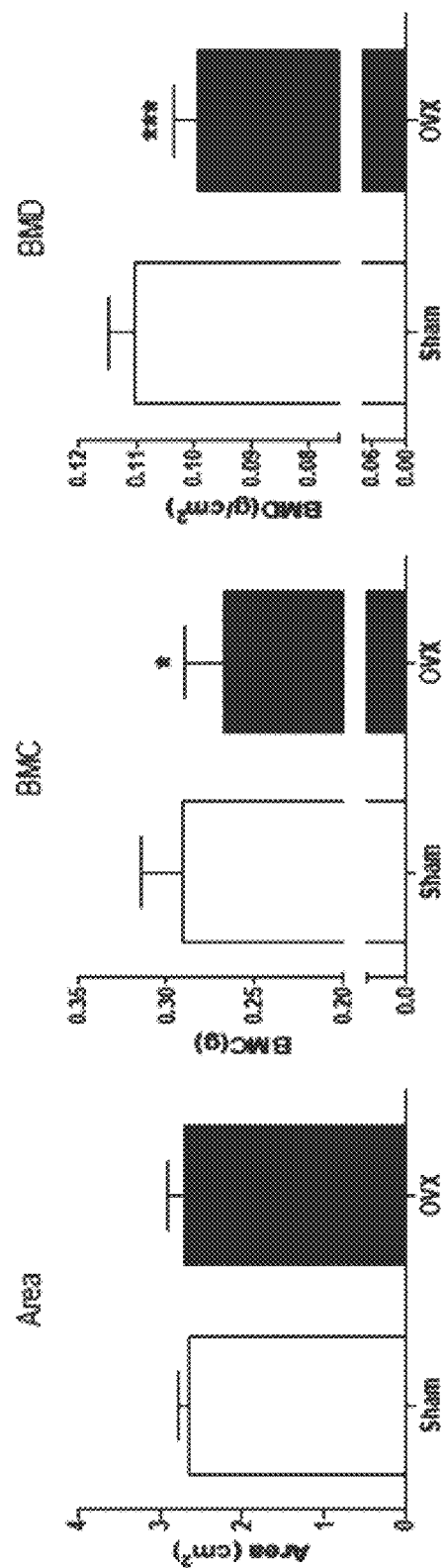
FIG. 2 shows a result of comparing the bone mineral density of the femoral region between a control (Sham) and an ovariectomy group (OVX) after female rats were subjected to ovariectomy (Area: area, BMC: bone mineral content, BMD: bone mineral density).

As a result, as shown in FIG. 2, it was confirmed that an area (Area) was equivalent in the Sham group and the OVX group without a difference, whereas BMC was significantly decreased in the OVX group, compared with the Sham group (*$p<0.05$) and as a BMD analysis result, BMD was also significantly decreased in the OVX group, compared with the Sham group (***$p<0.001$). This result is interpreted as an osteoporosis phenomenon which is one of the menopausal symptoms caused by ovariectomy, and can be used as an indicator for the establishment of a menopausal animal model together with an increase in body weight.

2-2. Confirmation of Changes in Organ Weight and Length

To examine a difference in the change in organ weight and length between the control (Sham) and the ovariectomy group (OVX) at the sacrifice of the rats 18 weeks after ovariectomy, the liver, spleen and large intestine were extracted and their weight and length were measured.

As a result, as shown in Table 1 below, it was confirmed that there was no difference in weights and lengths of the organs between the Sham group and the OVX group.

TABLE 1

| Group | Liver (g) | Spleen (g) | Large intestine (cm) |
|---|---|---|---|
| Sham (n = 10) | 7.863 ± 0.225 | 0.710 ± 0.021 | 17.050 ± 0.431 |
| OVX (n = 18) | 8.193 ± 0.233 | 0.696 ± 0.024 | 16.606 ± 0.327 |

2-3. Analysis of Blood Biochemical Index

To detect the blood biochemical index changed after ovariectomy, the rats were sacrificed 18 weeks after the ovariectomy, the concentrations of blood alkaline phosphatase (ALP), aspartate aminotransferase (AST), gamma-glutamyl transferase (GGT), glucose (GLU), total protein (TP), blood urea nitrogen (BUN) and creatinine (CRE) were comparatively measured using an automated blood chemistry analyzer (FUJI DRI-CHEM 3500s) after blood was obtained from the abdominal artery in the control (Sham) and the ovariectomy group (OVX).

Figure 3:
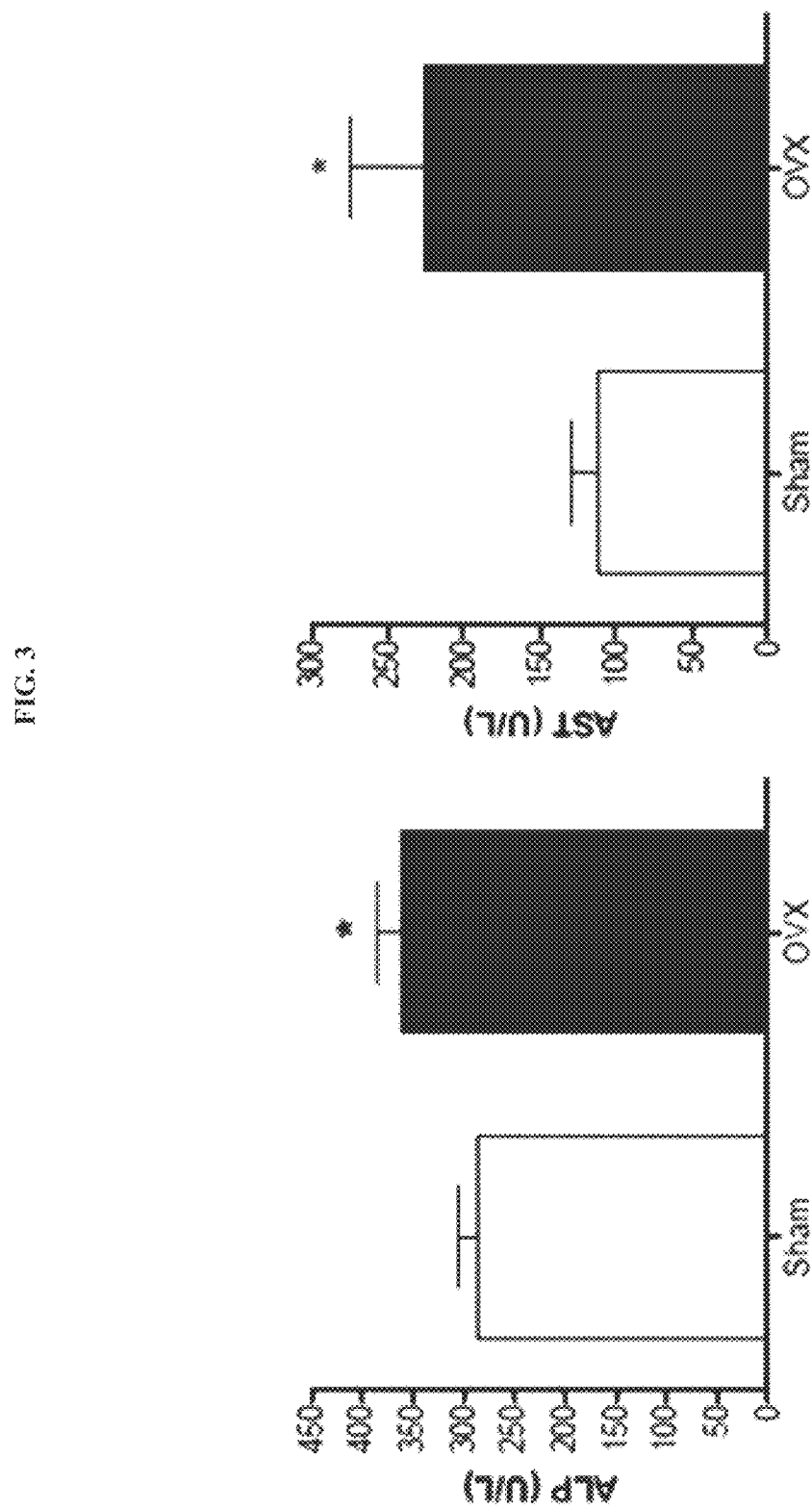
FIG. 3 shows a result of measuring blood alkaline phosphatase (ALP) and aspartic acid aminotransferase (AST) contents in blood obtained from a control (Sham) and an ovariectomy group (OVX) at week 18 after female rats were subjected to ovariectomy.

As a result, as shown in FIG. 3, in the OVX group, blood ALP and AST concentrations were 360.1±53.7 U/L and 226.4±127.0 U/L, respectively, which were significant increases of 26.3% and 50.9% compared with the Sham group (*p<0.05). ALP is the index useful for bone remodeling activity as it is an enzyme produced during osteogenesis by osteoblasts, and is increased in a bone disease. Since AST is abundantly distributed in the liver, its blood concentration is increased when liver cells are damaged. Therefore, the significant ALP and AST increases in the OVX group can indicate that the rats were in a similar metabolic condition which can appear in a menopausal woman due to hormone deficiency caused by ovariectomy. Meanwhile, as shown in Table 2, in the OVX group, the blood GGT concentration was increased approximately 43%, compared with the Sham group, which, however, was not statistically significant, and the blood GLU, TP, BUN and CRE concentrations were not changed, compared with the Sham group.

TABLE 2

| | Group | |
|---|---|---|
| Serum Parameter | Sham | OVX |
| GGT (U/L) | 4.1 ± 1.1 | 5.9 ± 3.8 |
| GLU (mg/dL) | 157.3 ± 40.0 | 154.9 ± 13.6 |
| BUN (mg/dL) | 15.3 ± 4.2 | 15.8 ± 3.4 |
| CRE (mg/dL) | 0.3 ± 0.1 | 0.2 ± 0.1 |
| TP (g/dL) | 6.0 ± 1.4 | 6.1 ± 0.2 |

2-4. Analysis of Blood Estradiol

To measure a blood estradiol level changed after ovariectomy, a rat was sacrificed 18 weeks after the ovariectomy by the same method as described in Example 2-3, blood was obtained from the control (Sham) and the ovariectomy group (OVX), and then measurement was performed using an Estradiol RIA kit (ES 180S-100, SIEMENS, Calbiotech Inc).

Figure 4:
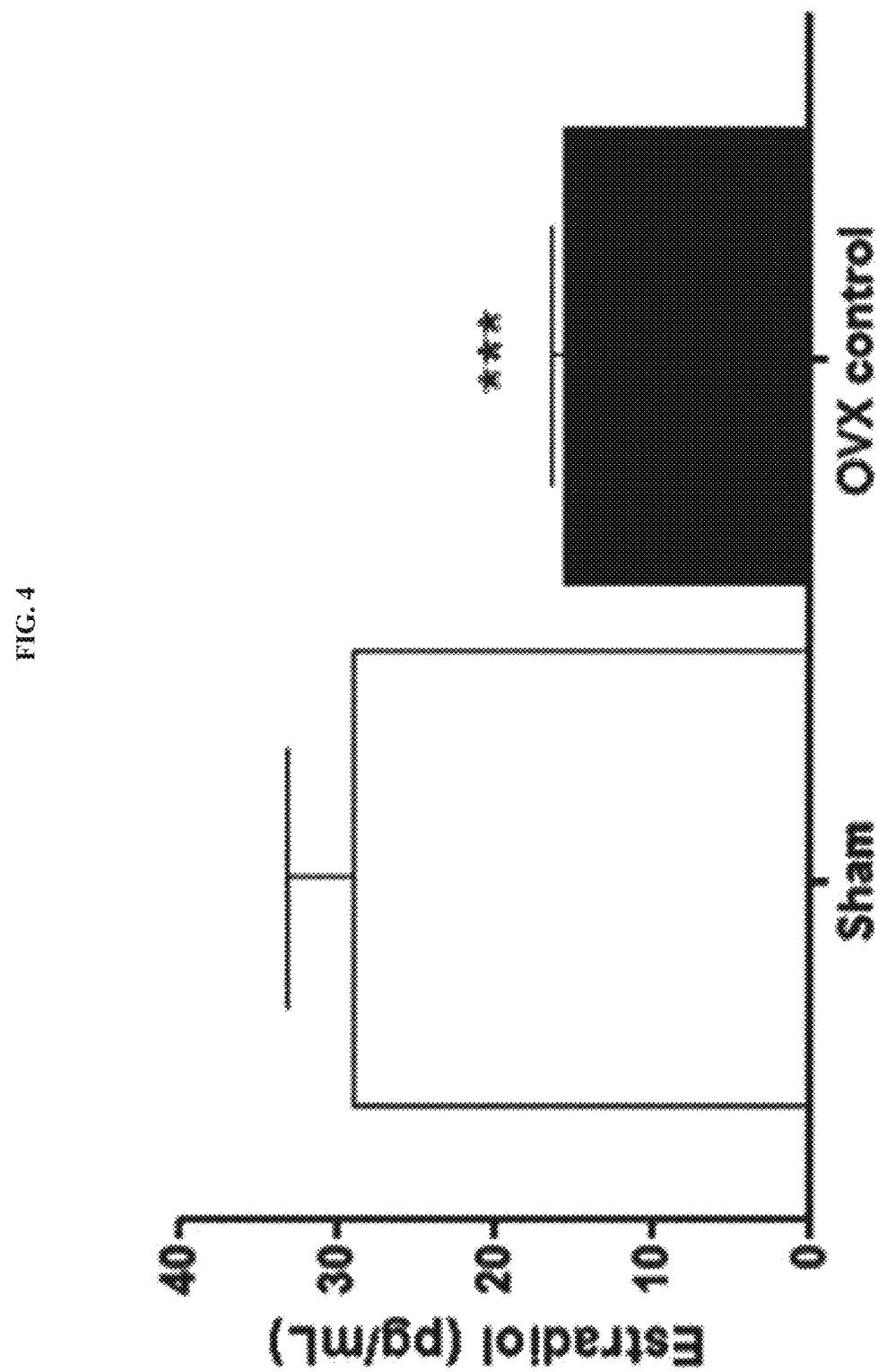
FIG. 4 shows a result of measuring a blood estradiol content in blood obtained from a control (Sham) and an ovariectomy group (OVX) at week 18 after female rats were subjected to ovariectomy.

As a result, as shown in FIG. 4, the blood estradiol concentration in the OVX group was 15.4±4.2 pg/mL, which was significantly decreased 47%, compared with the control group, and can demonstrate that the rats are in a similar metabolic condition which can appear in a menopausal woman due to hormone deficiency caused by ovariectomy.

2-5. Analysis of Cytokines in Immune System

The spleen and a Peyer's patch were removed from rats in dissection of the control (Sham) and the ovariectomy group (OVX) 18 weeks after the ovariectomy, single cells were separated therefrom and then cultured for 72 hours, and then the supernatant was obtained to be used in cytokine analysis. In the cell culture, Concanavalin A (2 μg/mL) was treated to activate T cells. The cytokine analysis used a Multi-Analyte LISArray for Rat Kit (Cat.336161, QIAGEN), and IL-1α, 1β, 2, 4, 6, 10, 12, 13, INF-γ, TNF-a, GM and RANTES levels were measured. In addition, after measurement of the cytokine concentrations, a degree of color development was compared to reanalyze cytokines showing a difference from the control.

Figure 5A:
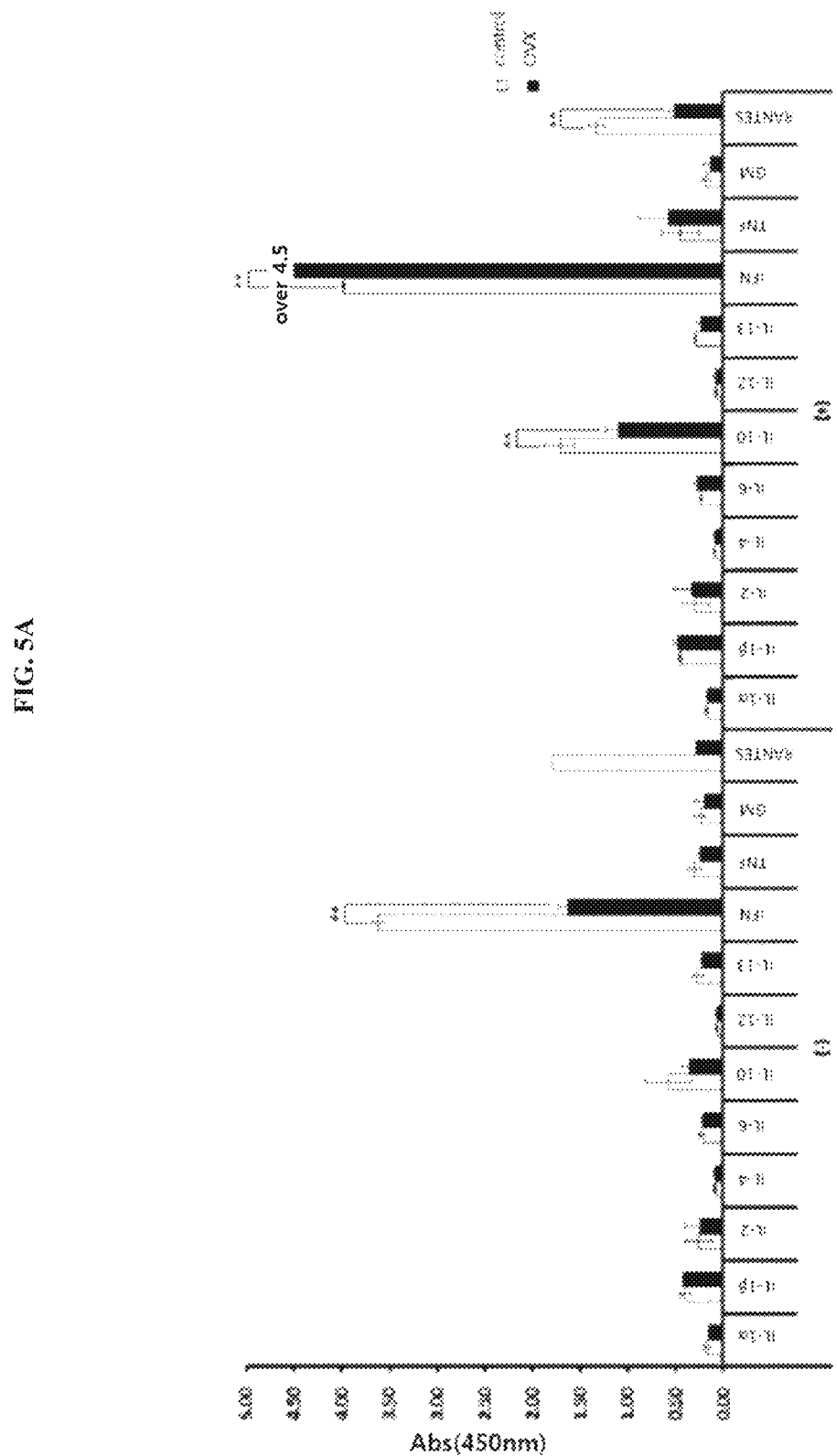

First, as a result of the analysis of cytokines in the Peyer's patch, as shown in FIG. 5A, it was confirmed that the anti-inflammatory cytokine IL-10 was decreased regardless of stimulation. Based on this, IL-10 was analyzed with the possibility of the anti-inflammatory effect of intestinal immunity and by focusing on the change in IL-10 in systemic immunity.

Figure 5B:
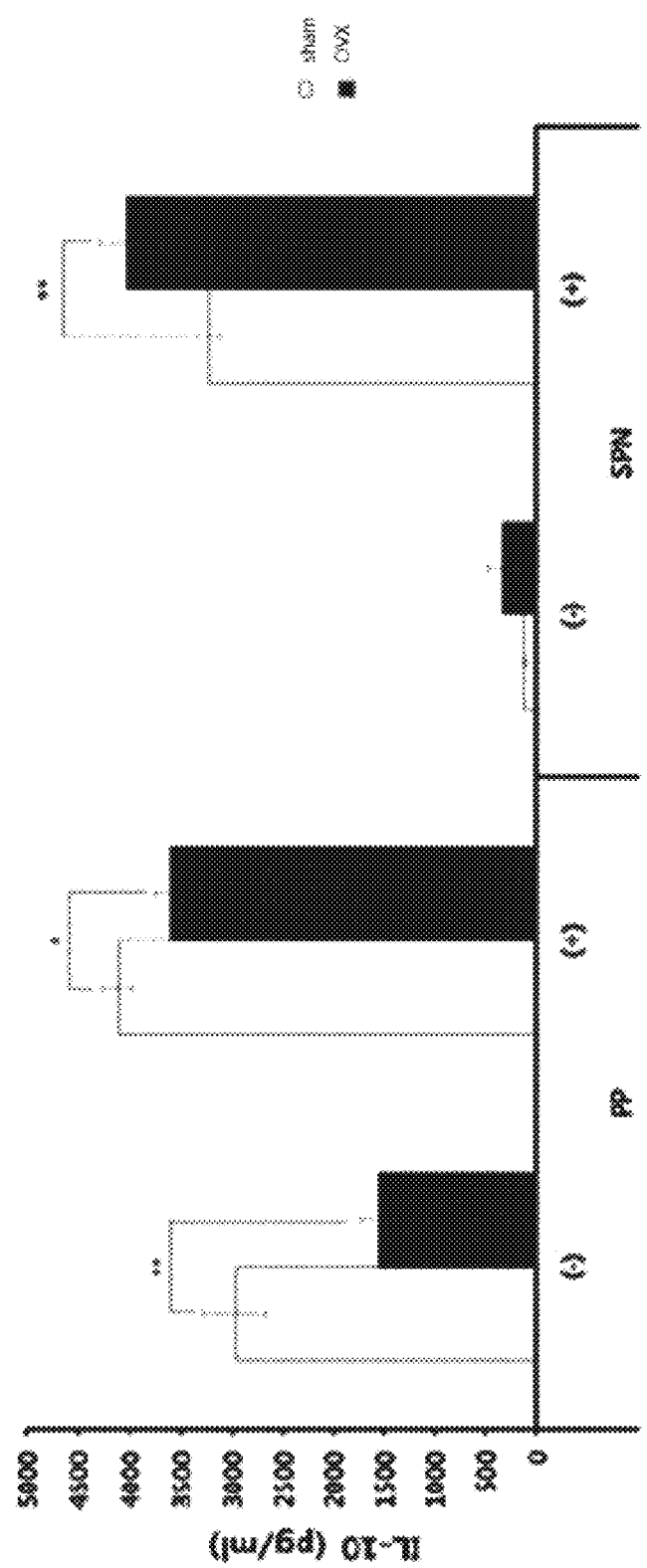

For the IL-10 analysis, a Rat IL-10 ELISA set (cat No. 555134, BD Biosciences) was used. As a result of the measurement, as shown in FIG. 5B, like the result of FIG. 5A, in the Peyer's patch, IL-10 was significantly reduced. On the other hand, as the result of the spleen measurement, different from the result in the Peyer's patch, IL-10 was significantly increased in the OVX group. Based on previous research, it was identified that there was a study on the increase in IL-10 and the possibility of inducing regulatory T cells in the systemic immunity in an ovariectomy model, and the increase in IL-10 and the possibility of inducing regulatory T cells were confirmed by comparing the present research result.

From the results, it was confirmed that a menopausal animal model was well established from female rats through ovariectomy, and the change in intestinal microorganisms according to menopause was to be analyzed using the model.

Example 3. Analysis of Change in Intestinal Microorganisms in Menopausal Animal Model Fecal samples of the control (Sham) and the ovariectomy group (OVX) obtained at corresponding periods of 0, 1, 3, 6, 10, 14, and 18 weeks after ovariectomy according to the method described in Example 1-1 were used in analysis of the change in intestinal microorganisms due to a decrease in estrogen caused by ovariectomy according to the method described in Example 1-6.

Figure 6:
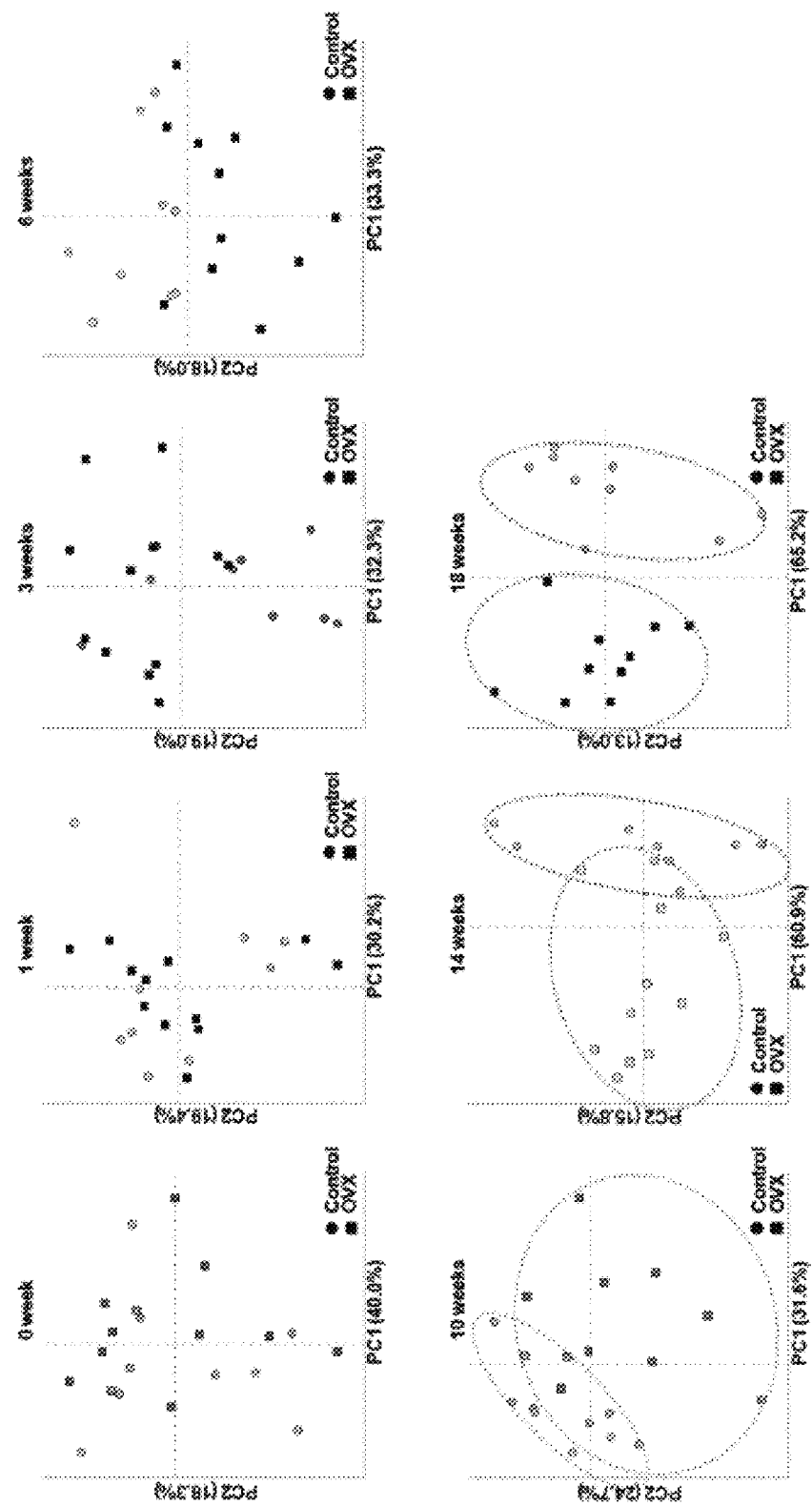
FIG. 6 shows a result of PCA plotting showing entire changes in intestinal microorganisms in a control (Sham) and an ovariectomy group (OVX) at week 0, 1, 3, 6, 10, 14 and 18 after female rats were subjected to ovariectomy.

As a result of confirming the change in total microorganisms over time in the OVX group and the Sham group through PCA plotting, as shown in FIG. 6, until 3 weeks, no difference in intestinal microorganisms between the OVX group and the Sham group was shown, from 6 weeks, the difference in intestinal microorganisms started to be identified, from 10 weeks, the separation of intestinal microorganisms between the OVX group and the Sham group was clearly shown, and after 18 weeks, the distribution of the intestinal microorganisms between two groups showed a separation pattern.

Further, as a result of analysis of the change in intestinal microorganisms at the species level, in the intestines of the OVX group and the Sham group, on average, 356 species of bacteria were present, and a relatively higher number of bacterial species were found in the OVX group, compared to the Sham group (the average of the Sham group: 324 species, the average of the OVX group: 387 species). Therefore, a statistical analysis was performed on each microbial species, and at week 18, microorganisms having a significant difference between the two groups were found. As a result, ultimately, 32 species of microorganisms were found, and among these, 22 species excluding 10 species of non-isolated microorganisms had been previously isolated. Table 3 shows that the distribution ratio of representative microorganisms showing a significant difference in the analysis of intestinal microorganisms in the menopausal animal model at week 18. In further detail, it was seen that, among the 32 species of microorganisms, 12 species were decreased in the OVX group, and 20 species were rather increased in the OVX group. Therefore, the microorganisms which seemed to be decreased in the OVX group were found/obtained, and used as menopause-alleviating intestinal microorganisms in the OVX group to conduct research. In addition, the pattern of change in key microorganisms over time was observed.

Figure 7:
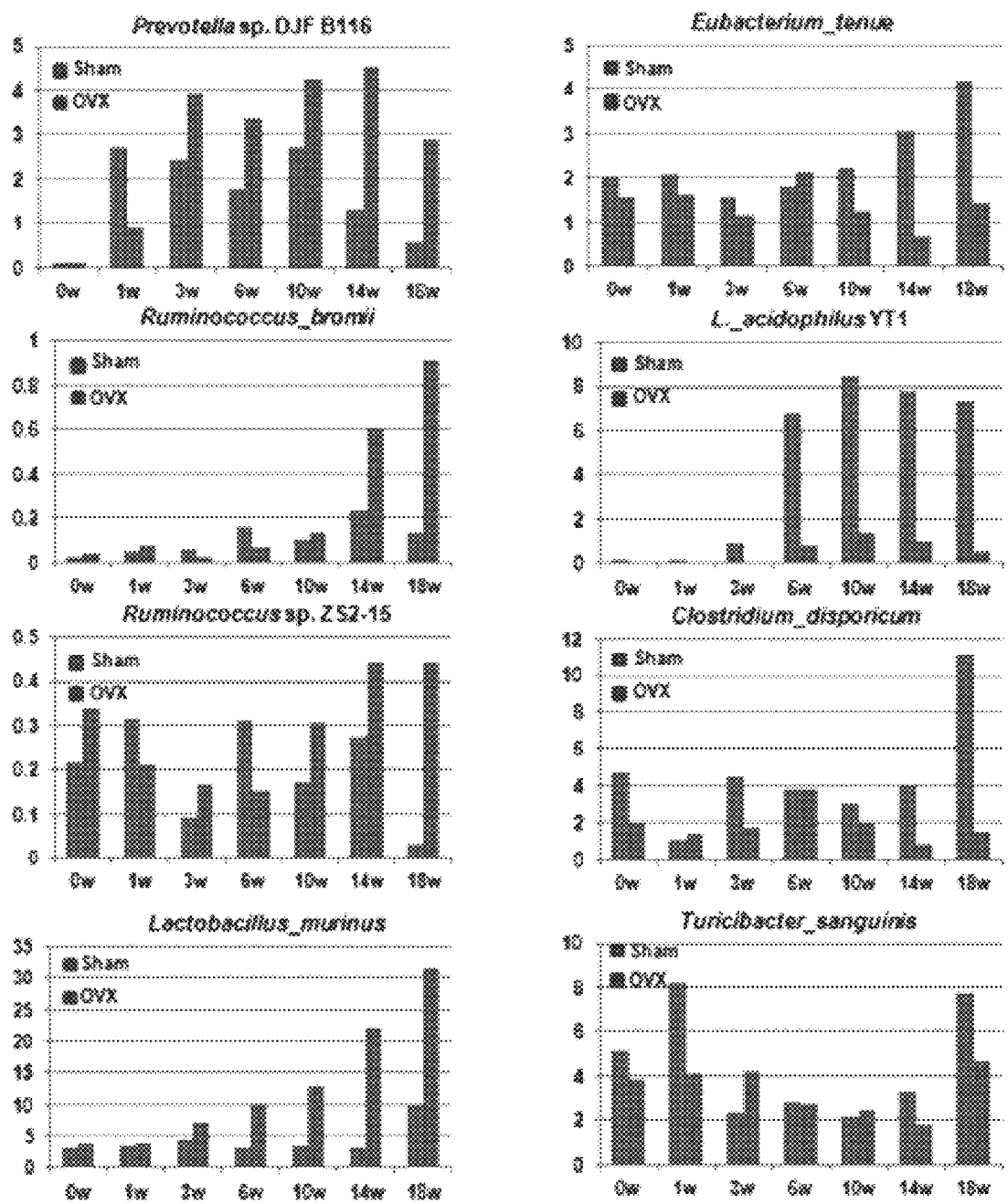
FIG. 7 shows a change in distribution of major microorganisms over time by analyzing a change in intestinal microorganisms at the species level at week 0, 1, 3, 6, 10, 14 and 18 after female rats were subjected to ovariectomy.

As a result, as shown in FIG. 7, microorganisms showing a dramatic change over a culturing period, for example, *Prevotella* sp. DJF B116, *Eubacterium_tenue*, *Ruminococcus_bromii*, *Lactobacillus acidophilus* YT1, *Ruminococcus* sp. ZS2-15, *Clostridium_disporicum*, *Lactobacillus_murinus*, and *Turicibacter_sanguinis* were able to be confirmed.

TABLE 3

| Closest bacteria | Sham | | OVX | | |
| --- | --- | --- | --- | --- | --- |
| | Mean (%) | STDV (%) | Mean (%) | STDV (%) | p-values |
| *Lactobacillus murinus* | 9.82 | 5.01 | 29.8 | 14.06 | 0 |
| *Lactobacillus johnsonii* | 1.85 | 1.85 | 3.67 | 2.88 | 0.069 |
| *Ruminococcus bromii* | 0.14 | 0.11 | 0.92 | 1.08 | 0.008 |
| *Marinilabilia salmonicolor* | 0.14 | 0.13 | 0.35 | 0.41 | 0.059 |
| *Papillibacter cinnamivorans* | 0.1 | 0.12 | 0.58 | 0.88 | 0.04 |
| *Clostridium indolis* | 0.03 | 0.07 | 0.43 | 0.53 | 0.007 |
| *Catabacter hongkongensis* | 0 | 0 | 0.04 | 0.06 | 0.015 |
| Uncultured swine fecal bacterium FPC63 | 0 | 0 | 0.12 | 0.21 | 0.024 |
| Uncultured bacterium ii1306 | 0 | 0 | 0.06 | 0.1 | 0.028 |
| *Clostridiales bacterium* DJF CP67 | 0 | 0 | 0.03 | 0.06 | 0.059 |
| *Clostridium disporicum* | 11.1 | 6.98 | 1.56 | 2.23 | 0.005 |
| *Lactobacillus acidophilus* | 7.4 | 9.58 | 0.58 | 1.41 | 0.079 |
| *Eubacterium tenue* | 4.18 | 2.41 | 1.42 | 1.66 | 0.013 |
| *Lactobacillus intestinalis* | 3.16 | 3.2 | 0.08 | 0.15 | 0.026 |
| *Clostridium lituseburense* | 2.32 | 1.06 | 1.19 | 1.83 | 0.064 |
| *Clostridium* sp. ID4 | 0.98 | 1.08 | 0.03 | 0.06 | 0.038 |
| Uncultured human intestinal firmicute CJ6 | 0.15 | 0.08 | 0.08 | 0.08 | 0.062 |
| *Clostridium* sp. BG-C36 | 0.12 | 0.13 | 0.01 | 0.03 | 0.034 |
| *Clostridiaceae bacterium* SH032 | 0.06 | 0.05 | 0.01 | 0.03 | 0.041 |
| *Helicobacter* sp. WYS-200112 | 0.05 | 0.05 | 0 | 0 | 0.035 |
| *Clostridium* sp. CYP2 | 0.05 | 0.05 | 0.01 | 0.02 | 0.062 |
| *Ruminococcus* sp. C047 | 0.04 | 0.05 | 0.15 | 0.13 | 0.006 |

Example 4. Discovery of Intestinal Microorganisms for Alleviating Menopausal Symptoms Based on the result of Example 3, among the microorganisms significantly decreased in the distribution in the ovariectomy group (OVX) compared with the control (Sham), as lactic acid bacteria, the microorganisms showing the biggest difference (present at 3% or more in the intestine, and two or more-fold qualitative difference between two groups), that is, *Lactobacillus acidophilus* were set as a target, and the isolation of the corresponding microorganisms was attempted by changing culture conditions such as an MRS/Rogosa medium, pH5/6.4, an aerobic/aerobic condition, etc. The corresponding microorganisms were isolated using 18-week feces of samples for confirming the change in intestinal microorganisms in the Sham group and the OVX group, single isolation of 101 microorganism colonies was performed, and then subjected to 16S rDNA sequencing to identify the corresponding microorganisms.

As a result, each of 8 species of microorganisms of the genus *Lactobacillus*, for example, 23 strains of *Lactobacillus reuteri*, 38 strains of *Lactobacillus johnsonii*, *Lactobacillus animalis*, *Lactobacillus vaginalis*, *Lactobacillus pontis*, *Lactobacillus taiwanensis*, *Lactobacillus intestinalis*, and *Lactobacillus acidophilus* set as a target, was isolated. The isolated *Lactobacillus acidophilus* strain is a novel stain, which was named *Lactobacillus acidophilus* YT1, which was deposited in the Korean Culture Center of Microorganisms (KCCM) (Deposition Number KCCM11808P).

Example 5. Verification of Efficacy of Alleviating Menopause According to Administration of *Lactobacillus acidophilus* Strain To examine an effect of alleviating menopausal symptoms by *Lactobacillus acidophilus* using the target candidate intestinal microorganisms, that is, the *Lactobacillus acidophilus* YT1 strain, which was isolated in Example 4, and another conventionally known strain of *Lactobacillus acidophilus* (KCTC 3164), an experiment was carried out by the following method using a menopausal animal model prepared by the method described in Example 1-1.

Normalization of intestinal microorganisms in experimental animals was carried out by rotating 4-week-old female rats for 4 weeks, and then ovariectomy was performed 8 weeks after birth. As described above, the novel *Lactobacillus acidophilus* strain isolated from the rat feces and the known strain were used to design an experiment, and the experimental groups were divided into a total of 5 groups: 1) the control (Sham)+PBS (n=10); 2) the ovariectomy group (OVX)+PBS (n=10); 3) the ovariectomy group (OVX)+20 µg/kg of estradiol (n=10); 4) the ovariectomy group (OVX)+*Lactobacillus acidophilus* (*L. acidophilus*) KCTC 3164 (n=11); and 5) the ovariectomy group (OVX)+*Lactobacillus acidophilus* (*L. acidophilus*) YT1 (n=11) for the experiment. All samples were administered once every two days, samples of intestinal microorganisms were orally administered at a dose of $1 \times 10^9$ CFU/mL/head, and estradiol was intraperitoneally administered at a dose of 20 µg/kg/3 mL.

5-1. Analysis of Changes in Body Weight and Body Fat Mass

Estradiol or each *Lactobacillus acidophilus* strain was administered into rats of each experimental group for 16 weeks from 1 week after ovariectomy according to the above-described method, and a body weight was measured every week.

Figure 8:
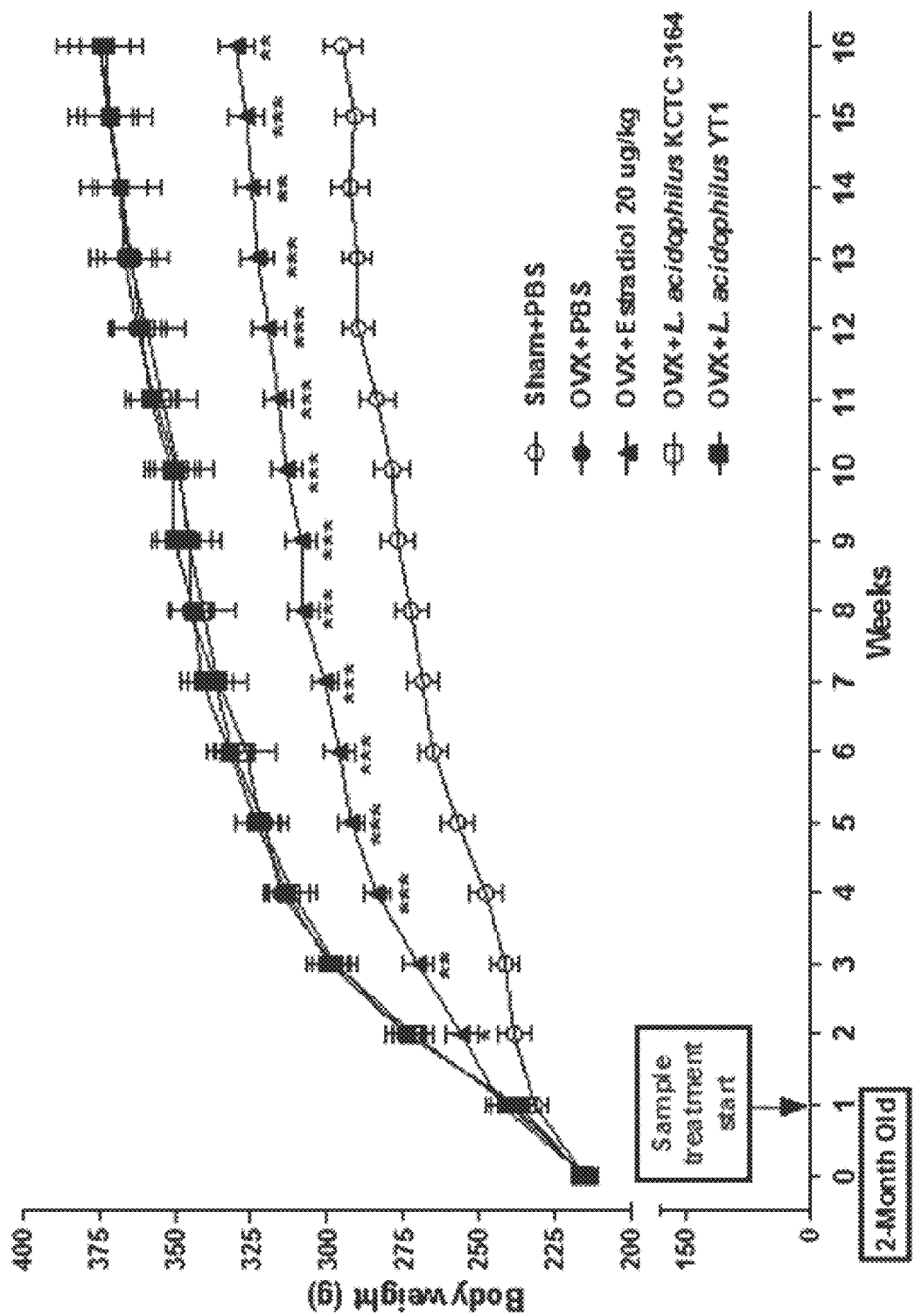
FIG. 8 shows changes in body weight over time in each experimental group after ovariectomy in order to evaluate an effect of alleviating menopausal symptoms by administration of *Lactobacillus acidophilus*.

As a result, as shown in FIG. 8, the body weights of the ovariectomy group (OVX+PBS) and the *Lactobacillus acidophilus*-administered OVX group (OVX+*L. acidophilus* KCTC 3164, OVX+*L. acidophilus* YT1) were significantly increased (*p<0.001) continuously from two weeks after ovariectomy, compared with that of the control (Sham+PBS). The body weight of the estradiol-administered group (OVX+Estradiol) was significantly decreased (*p<0.001), compared with the OVX group. After surgery, the increase in body weight means that the OVX animal model was well established.

Figure 9:
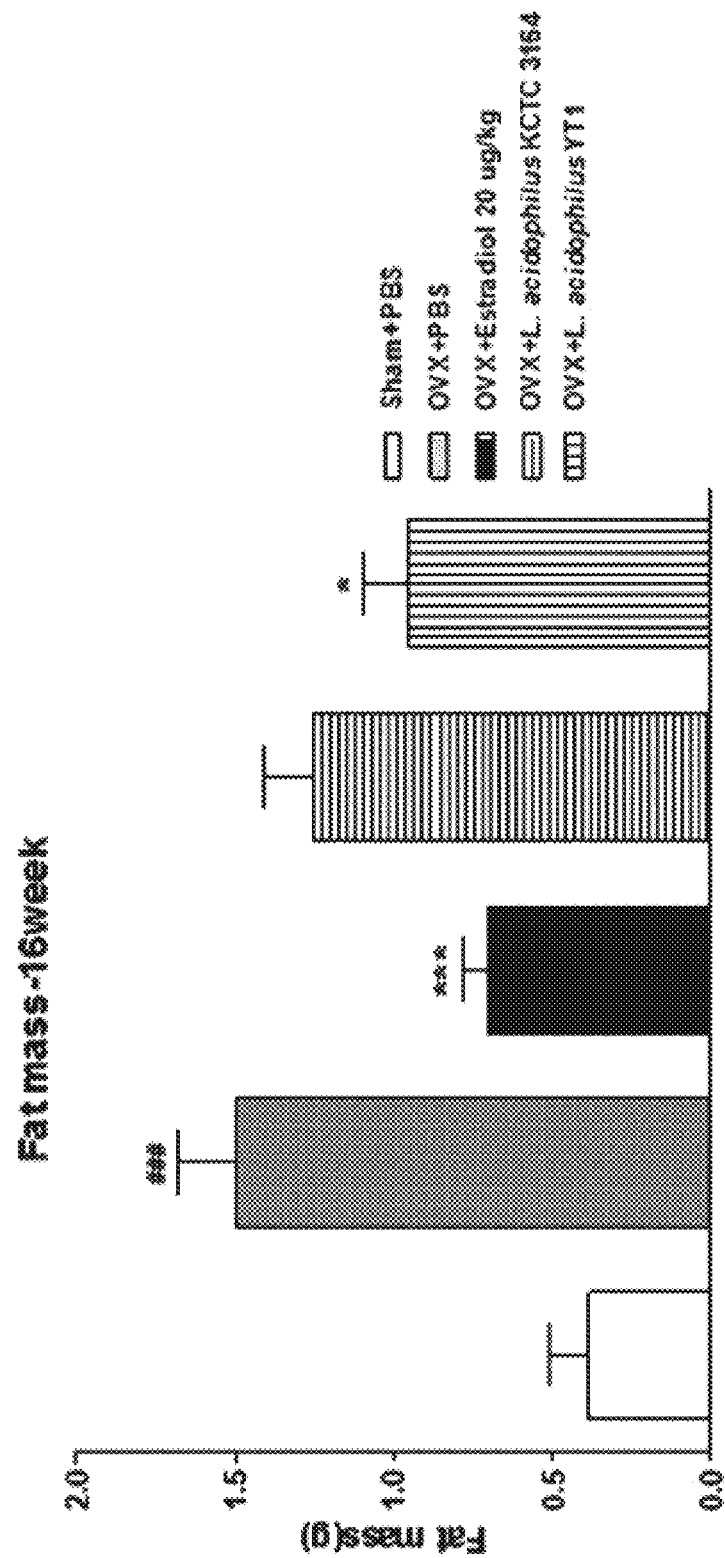
FIG. 9 shows a body fat mass in each experimental group measured at week 16 after ovariectomy in order to evaluate an effect of alleviating menopausal symptoms by administration of *Lactobacillus acidophilus*.

Subsequently, as a result of analyzing a body fat mass in the femoral region 16 weeks after ovariectomy, as shown in FIG. 9, it was confirmed that the body fat mass of the OVX+PBS group was significantly increased, compared with the Sham+PBS group, and it was confirmed that the body fat mass of the estradiol-administered group (OVX+Estradiol) and the novel *Lactobacillus acidophilus* strain-administered group (OVX+*L. acidophilus* YT1) were significantly decreased, compared with the OVX+PBS group.

5-2. Analysis of Change in Eating Behavior

To evaluate the change in eating behavior according to the administration of *Lactobacillus acidophilus* in a menopausal animal model, feed and water intakes were confirmed for 16 weeks from 1 week of ovariectomy.

Figure 10A:
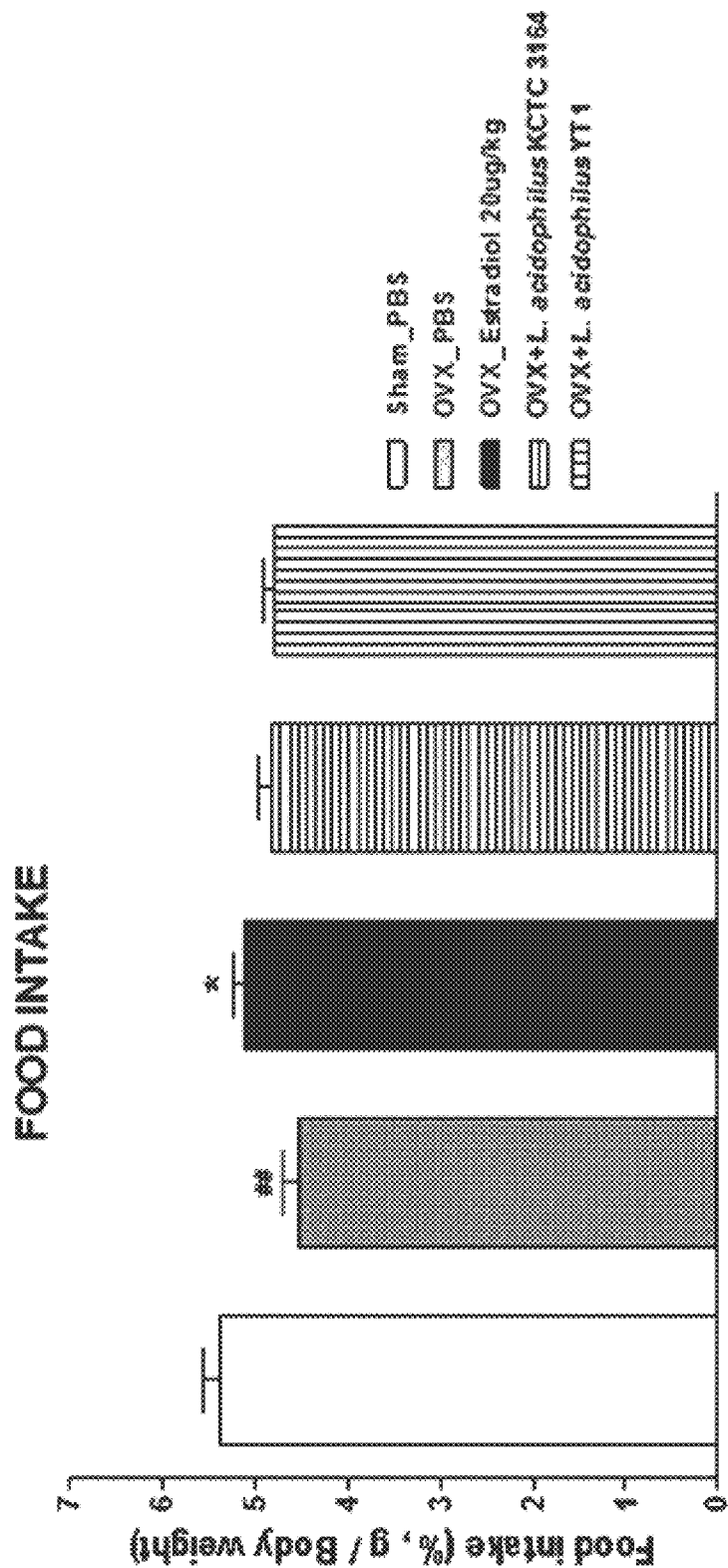
FIGS. 10A and 10B show a result of measuring food intake (FIG. 10A) and water intake (FIG. 10B) of each experimental group from week 1 to week 16 after ovariectomy in order to evaluate an effect of alleviating menopausal symptoms by administration of *Lactobacillus acidophilus*.

First, as a result of eating behavior analysis, as shown in FIG. 10A, compared with the control (Sham+PBS), in the ovariectomy group (OVX+PBS), food intake was decreased, and compared with the ovariectomy group, in the estradiol-administered group (OVX+Estradiol), food intake was significantly increased, and in the *Lactobacillus acidophilus*-administered groups, slightly increased food intake was shown.

Figure 10B:
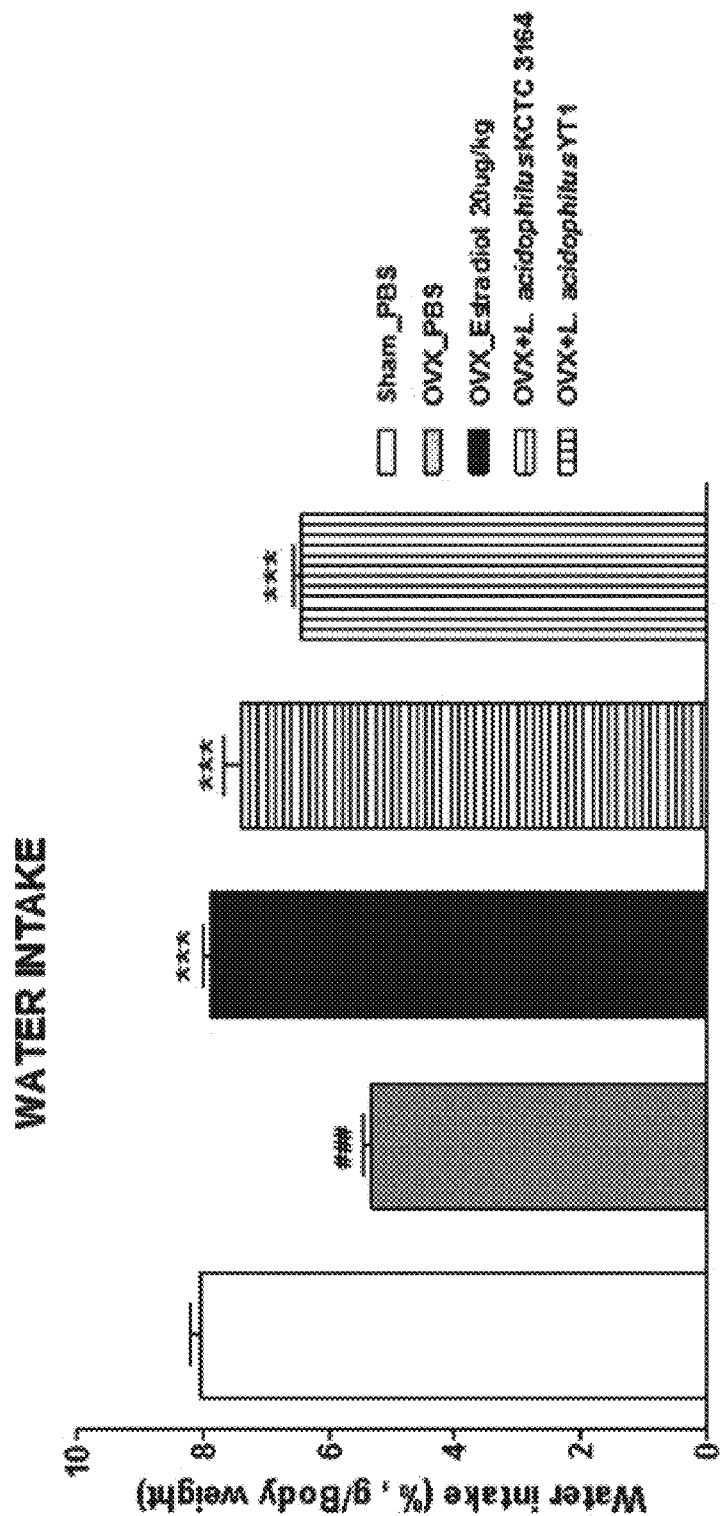

In terms of water intake, as shown in FIG. 10B, compared with the control (Sham+PBS), in the ovariectomy group (OVX+PBS), water intake was considerably reduced, whereas in the estradiol-administered group (OVX+Estradiol) and all of the *Lactobacillus acidophilus*-administered groups, water intake was significantly increased. This result showed that the reduction in eating behavior due to menopausal symptoms and pain caused by ovariectomy was improved by the influence of *Lactobacillus acidophilus*.

5-3. Analysis of Femoral Bone Mineral Density

In addition to the result of the example, it was examined whether a femoral bone mineral density was increased by the administration of *Lactobacillus acidophilus*. To this end, after ovariectomy, rats in each group was subjected to inhalation anesthesia 8, 12 and 16 weeks after the surgery, and a femoral bone mineral density (BMD) was measured using a bone densitometer (pDEXATM, Norland).

Figure 11A:
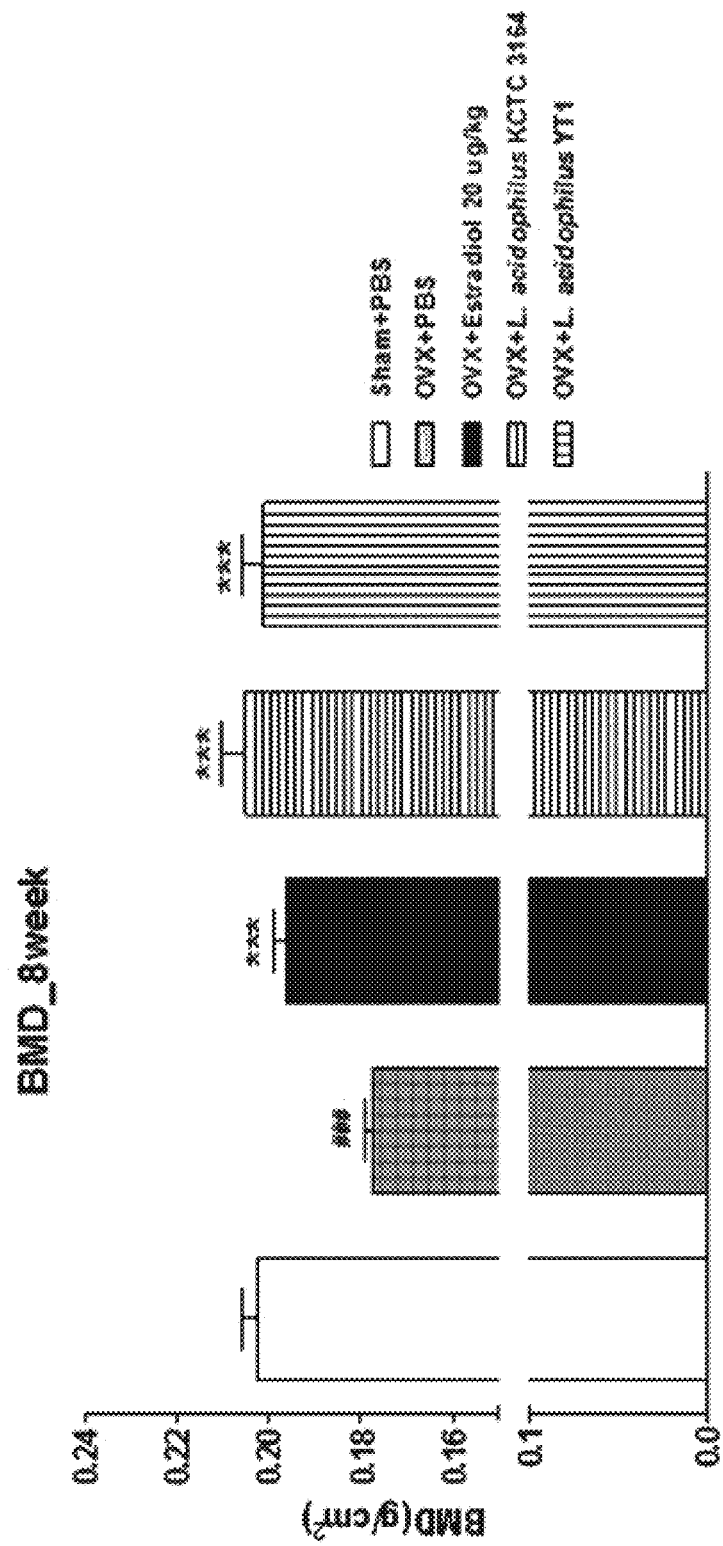
FIGS. 11A to 11C show a result of measuring a femoral bone mineral density at week 8 (FIG. 11A), 12 (FIG. 11B) and 16 (FIG. 11C) in each experimental group after ovariectomy in order to evaluate an effect of alleviating menopausal symptoms by administration of *Lactobacillus acidophilus*.
Figure 11B:
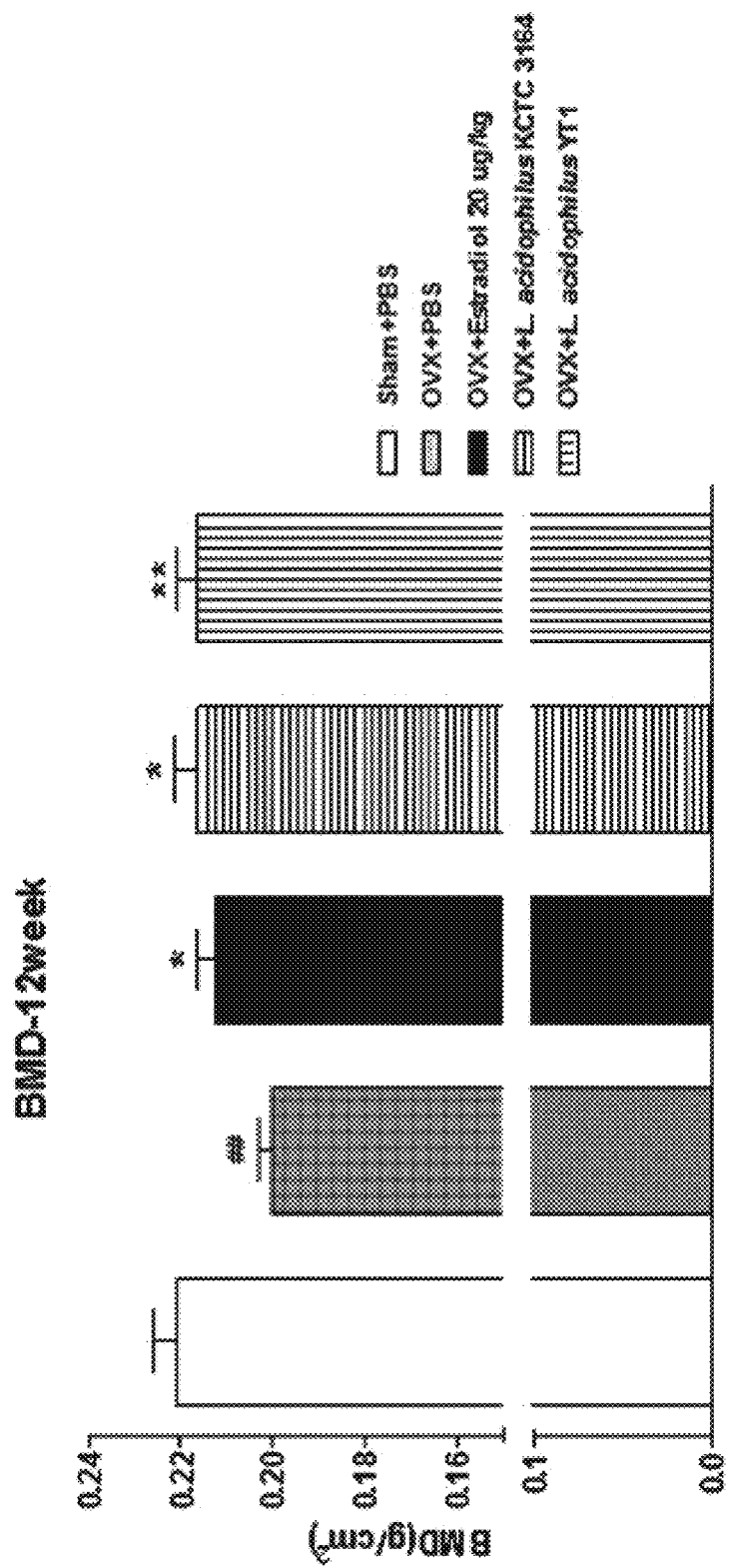
Figure 11C:
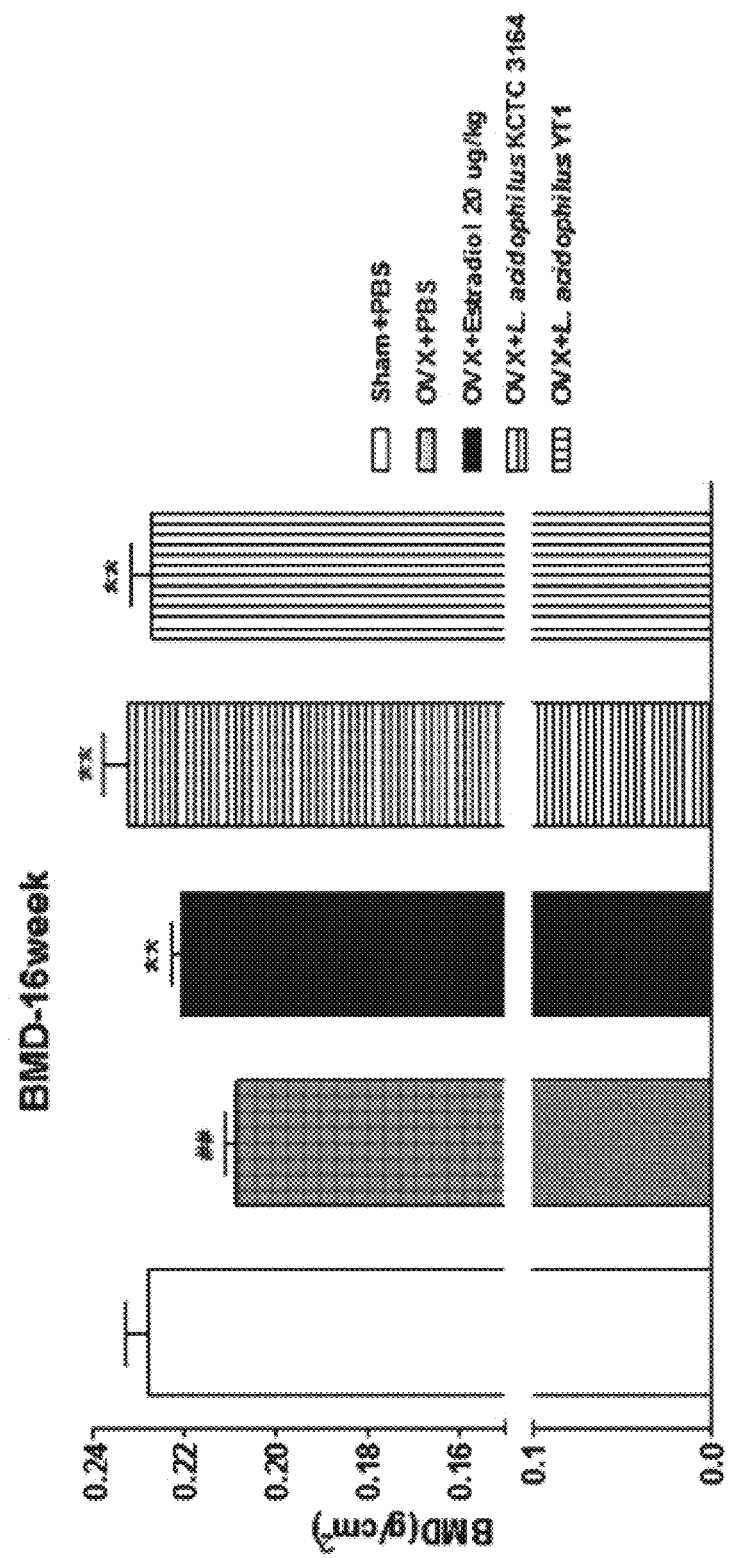
Figure 12A:
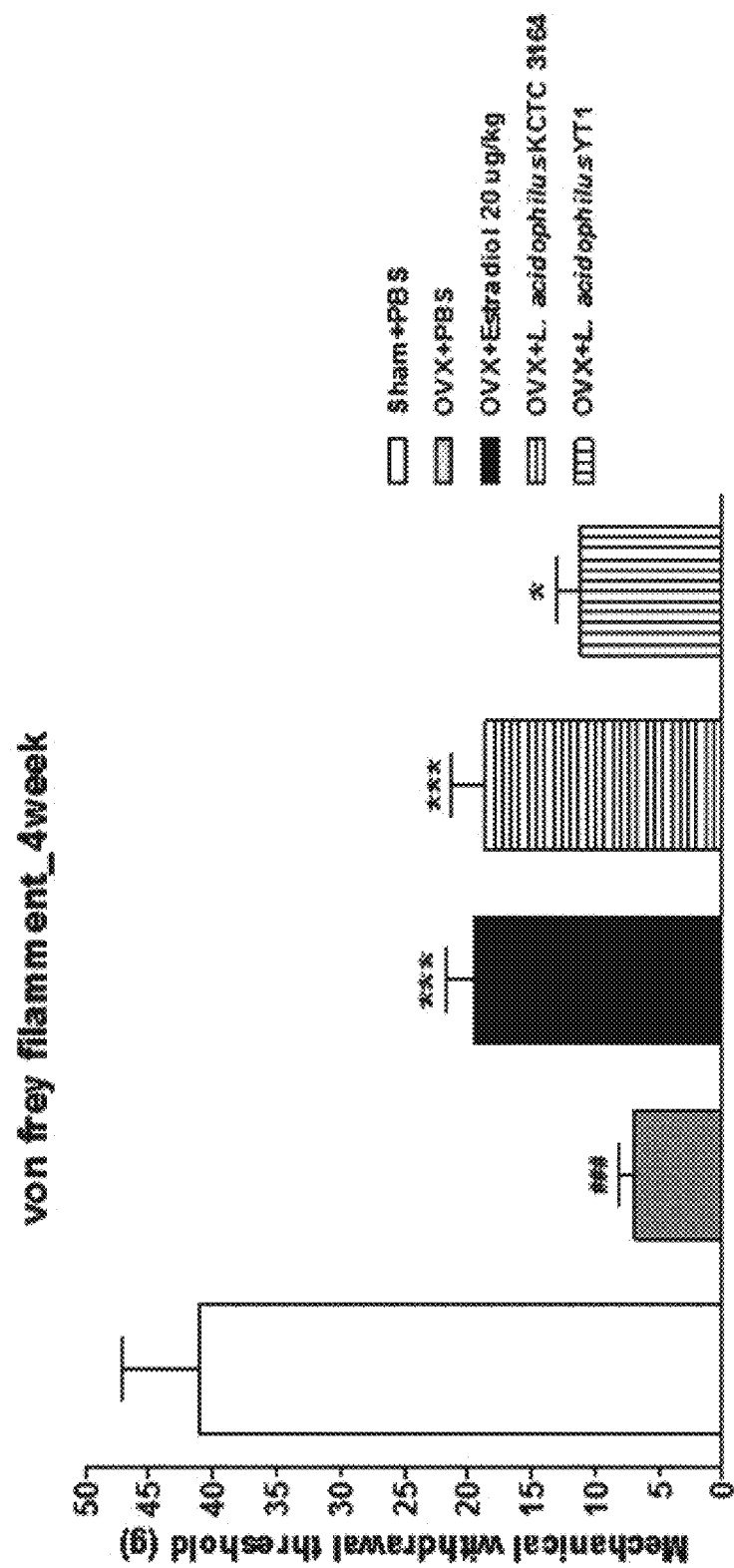
FIGS. 12A to 12D show pain sensitivity measured by performing a von Frey filament test for each experimental group at week 4 (FIG. 12A), 8 (FIG. 12B), 12 (FIG. 12C), and 16 (FIG. 12D) after ovariectomy in order to evaluate an effect of alleviating menopausal symptoms by administration of *Lactobacillus acidophilus*.
Figure 12B:
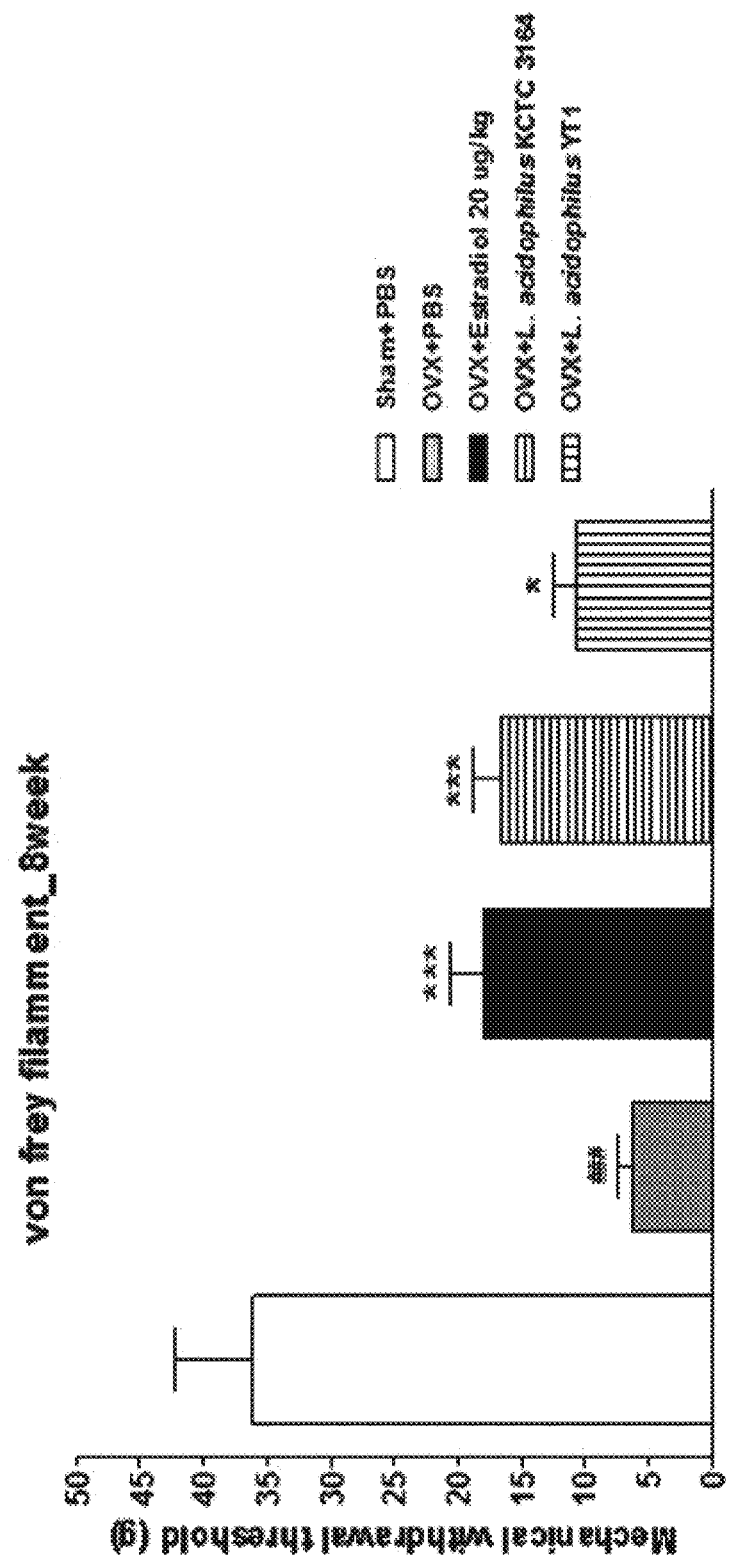
Figure 12C:
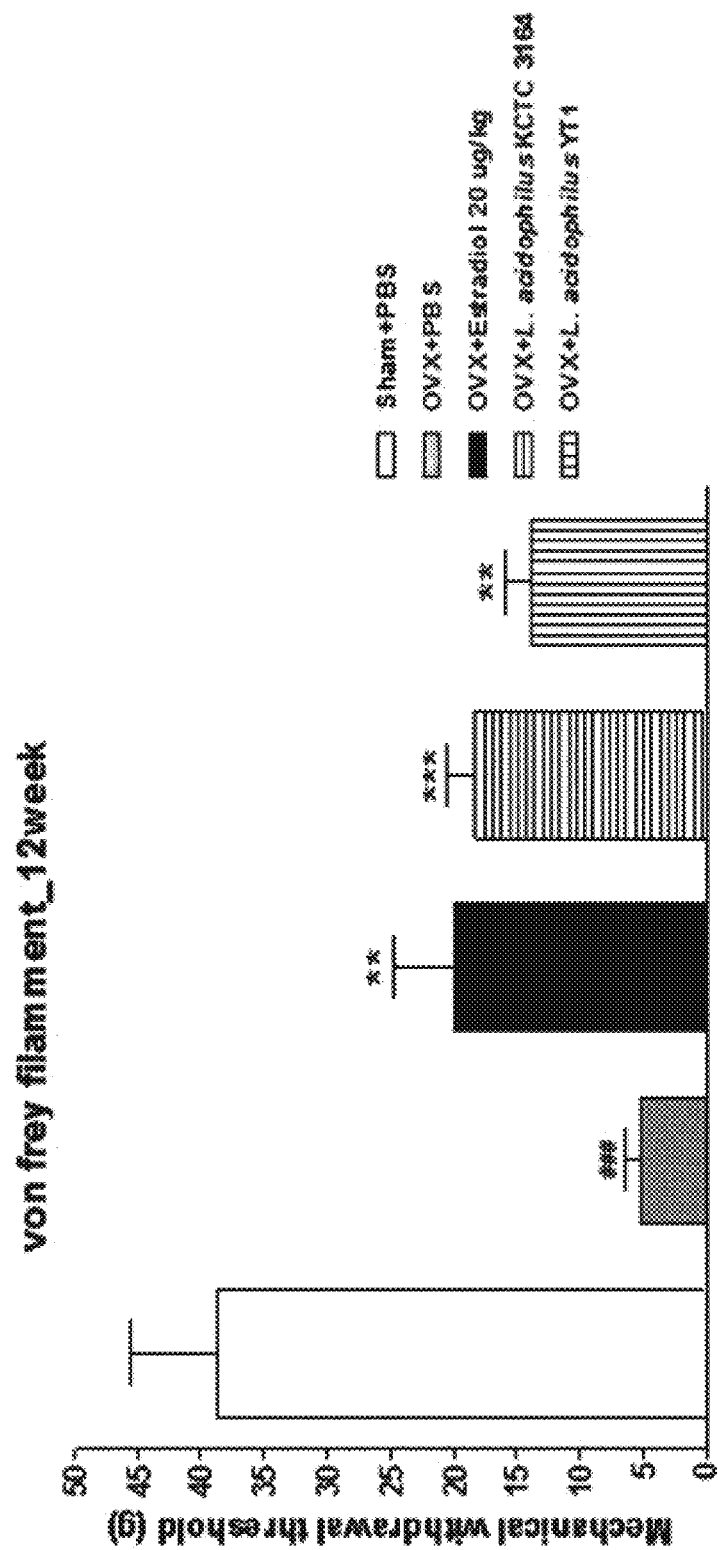
Figure 12D:
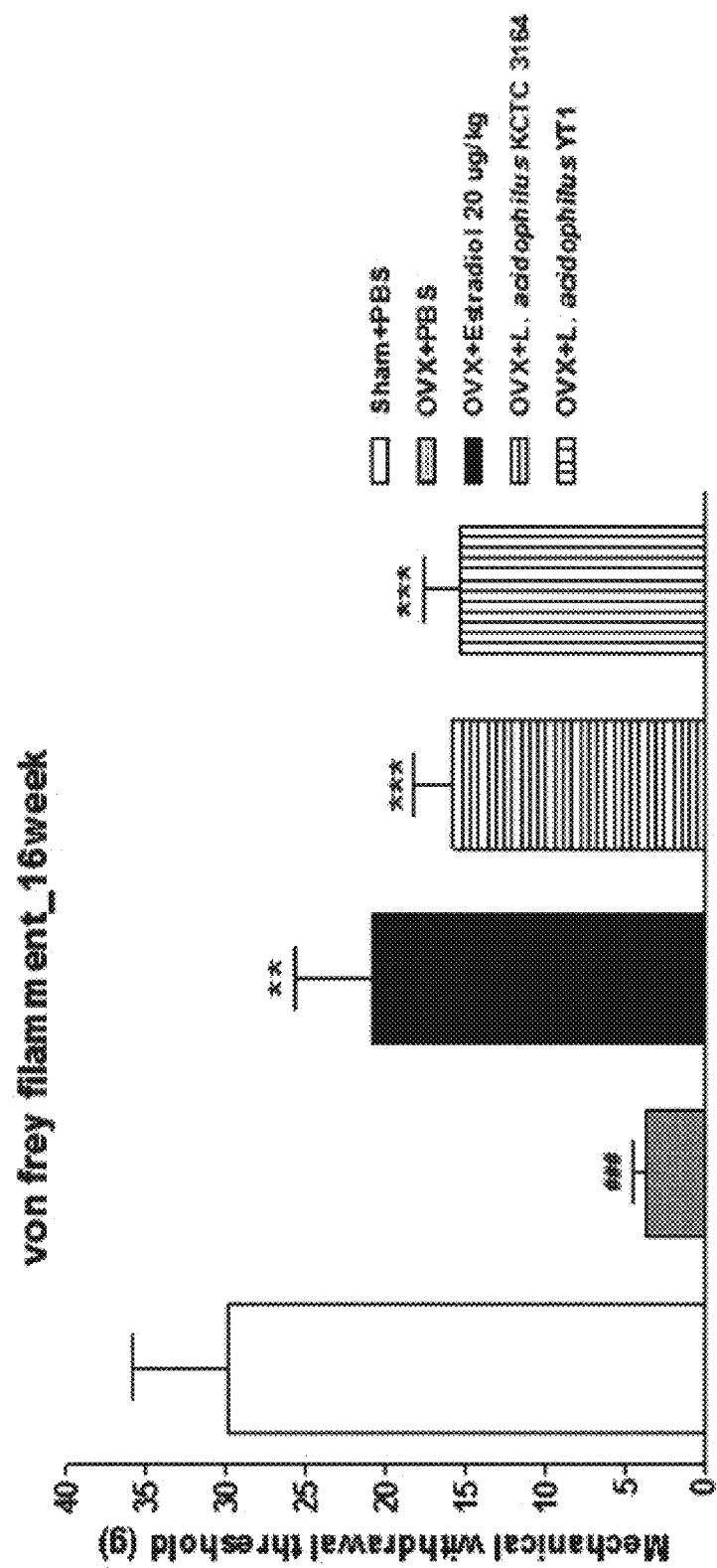

As a result, as shown in FIGS. 11A to 11C, in the ovariectomy group (OVX+PBS), compared with the control (Sham+PBS), the bone mineral density was continuously decreased from 8 until 16 weeks after ovariectomy. On the other hand, in the estradiol-administered group (OVX+Estradiol) and all of the *Lactobacillus acidophilus*-administered groups, compared with the ovariectomy group, it was confirmed that the bone mineral density was significantly increased at week 8, 12 and 16.

5-4. Analysis of Pain Sensitivity

According to a conventionally-studied report, it is known that, after ovariectomy, the mechanical withdrawal threshold (g), that is, pain sensitivity, was increased. Therefore, to confirm the change in pain sensitivity by the administration of *Lactobacillus acidophilus* in a menopausal animal model, a von Frey filament test was performed 4, 8, 12 and 16 weeks after the ovariectomy according to the method described in Example 1-4 to measure pain sensitivity.

As shown in FIGS. 12A to 12D, the test result showed that, compared with the control (Sham+PBS), in the ovariectomy group (OVX+PBS), pain sensitivity was increased by a significant decrease (p<0.001) in the threshold of a force at which pain was felt. On the other hand, in the estradiol-administered group (OVX+Estradiol) and all of the *Lactobacillus acidophilus*-administered groups, compared with the ovariectomy group, a threshold of the force at which pain was felt was significantly increased, indicating a decrease in pain sensitivity.

5-5. Analysis of Depression-Like Behavior

To examine whether depression caused by menopausal symptoms is improved by the administration of *Lactobacillus acidophilus*, a forced swim test was performed by the method described in Example 1-5 to examine whether depression-like behavior is shown 16 weeks after ovariectomy.

Figure 13A:
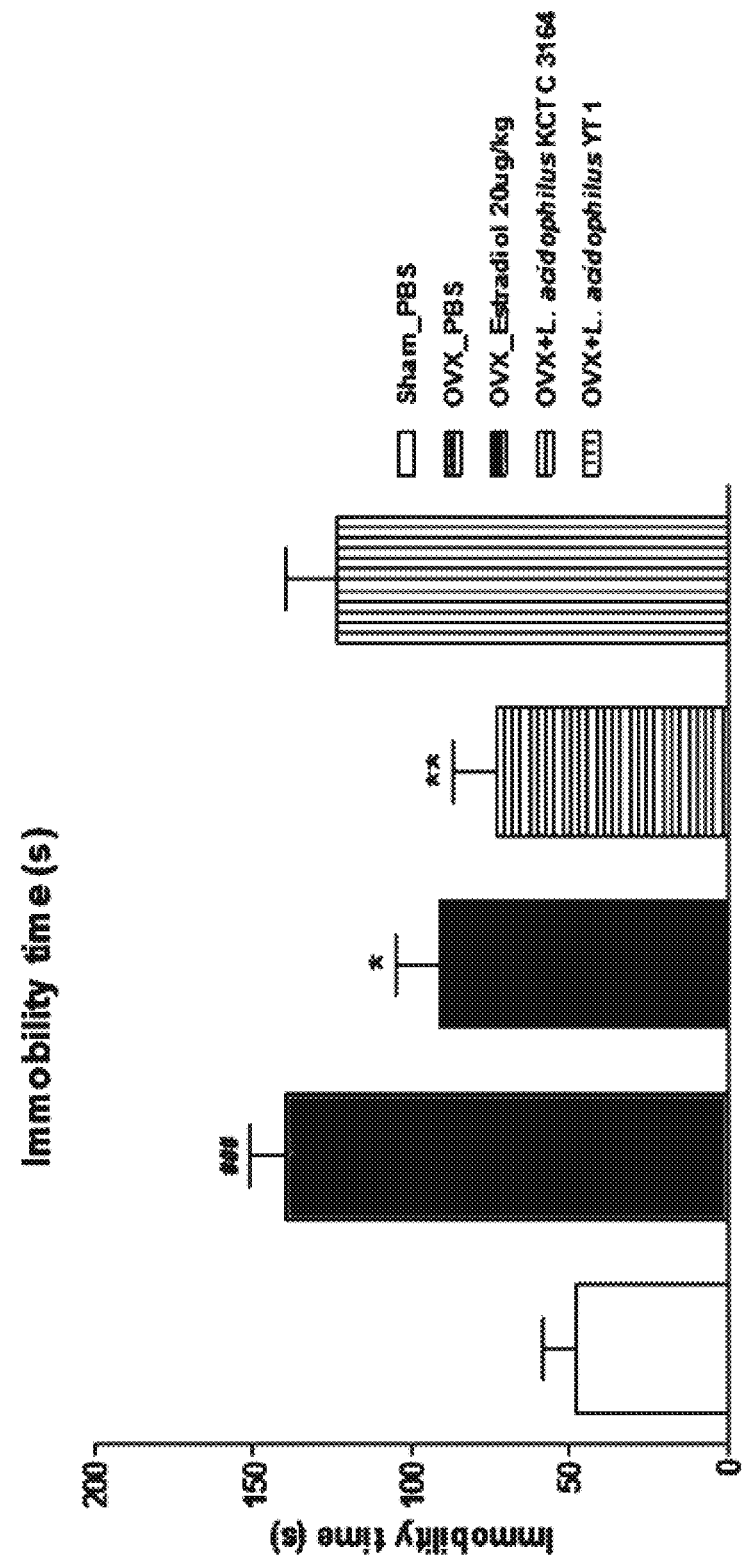
FIGS. 13A and 13B show immobility time (FIG. 13A) and swimming time (FIG. 13B) measured by performing a behavioral experiment by a forced swimming test for each experimental group at week 16 after ovariectomy in order to evaluate an effect of alleviating menopausal symptoms by administration of *Lactobacillus acidophilus*.
Figure 13B:
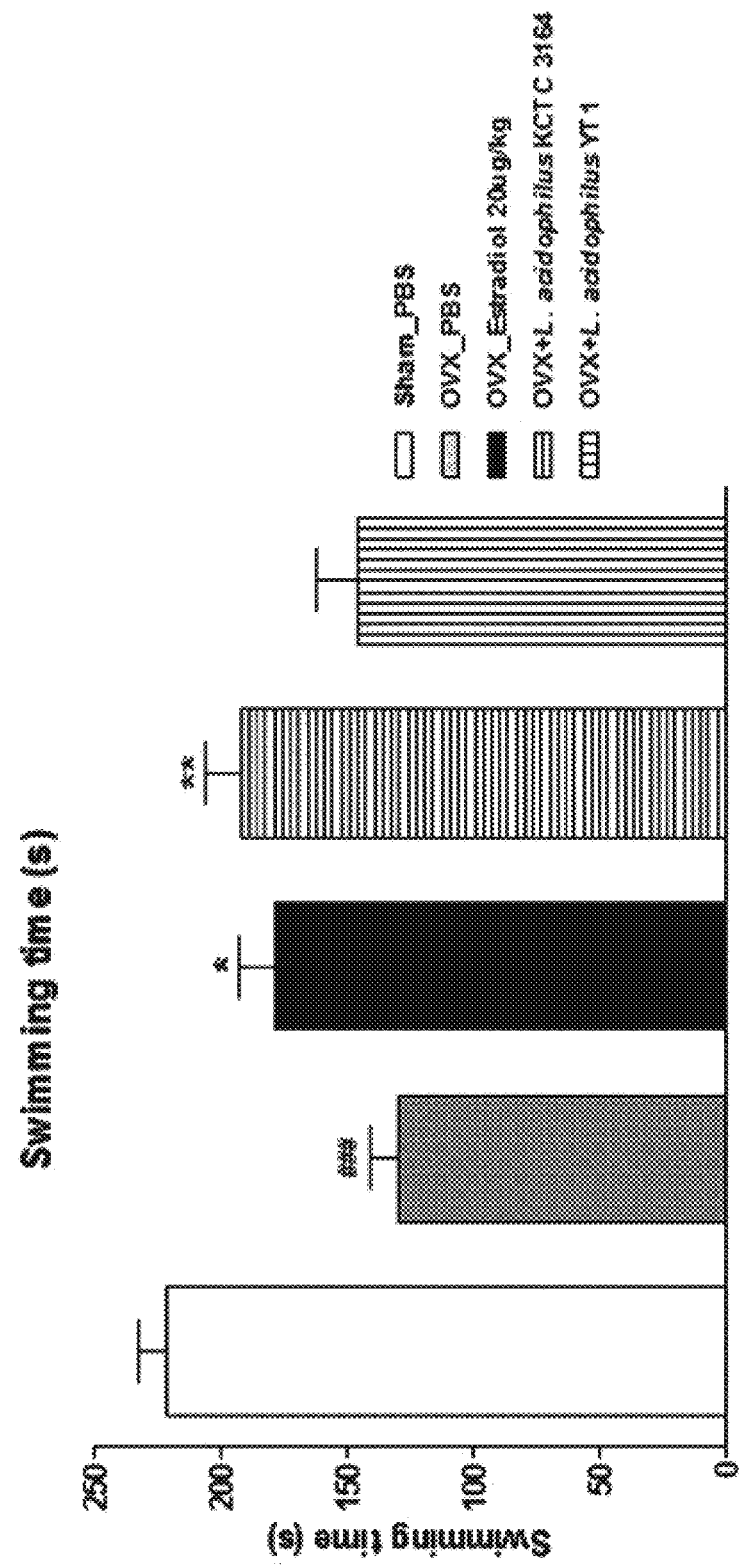

As shown in FIGS. 13A and 13B, the test result showed that, compared with the control (Sham+PBS), in the ovariectomy group (OVX+PBS), immobility time was increased, and swimming time was significantly decreased. On the other hand, in the estradiol-administered group (OVX+Estradiol) and the known *Lactobacillus acidophilus*-administered group (OVX+*L. acidophilus* KCTC 3164), compared with the ovariectomy group, the immobility time was significantly decreased, and the swimming time was increased. In addition, it was confirmed that the immobility time and the swimming time were rather slightly changed in the new strain *Lactobacillus acidophilus*-administered group (OVX+*L. acidophilus* YT1) isolated from rat feces. This result demonstrates that depression-like behavior shown by hormone deficiency caused by ovariectomy was improved by the administration of *Lactobacillus acidophilus*.

It was confirmed that, in all menopausal animal models, both of the known strain and the novel *Lactobacillus acidophilus* strain showed an effect of alleviating menopausal symptoms through the ovariectomy, and these results demonstrated a menopausal symptom-alleviating effect of the *Lactobacillus acidophilus* strain.

Example 6. Comparison of Efficacy Between *Lactobacillus acidophilus* Strain and Strain of Different Species of the Genus *Lactobacillus*

An experiment was performed by the following method using menopausal animal models to compare the efficacy of the *Lactobacillus acidophilus* strain verified according to Example 5 and the efficacy of the strain of a different species of the genus *Lactobacillus* (*L. reuteri*).

Normalization of intestinal microorganisms in experimental animals were carried out by rotating 9-week-old female rats for 3 weeks, and then ovariectomy was performed 12 weeks after birth. The experimental groups were divided into a total of 4 groups: 1) the control (Sham)+PBS (n=9); 2) the ovariectomy group (OVX)+PBS (n=10), 3) the ovariectomy group (OVX)+3.7×10$^6$/head/day of *L. reuteri* (n=10); and 4) the ovariectomy group (OVX)+3.7×10$^5$/head/day of *L. acidophilus* YT1 (n=10). All samples were orally administered once a day, and as shown in the experimental groups, *Lactobacillus reuteri* was orally administered at a dose 10-fold higher than *Lactobacillus acidophilus* YT1.

6-1. Analysis of Femoral Bone Mineral Density

To compare the efficacy of a *Lactobacillus acidophilus* strain with that of the strain of a different species of the genus *Lactobacillus* (*Lactobacillus reuteri* (*L. reuteri*)) in menopausal animal models, after ovariectomy, rats at week 12 of sample administration were subjected to inhalation anesthesia, and a femoral bone mineral density (BMD) was measured using a bone densitometer (pDEXATM, Norland).

Figure 14A:
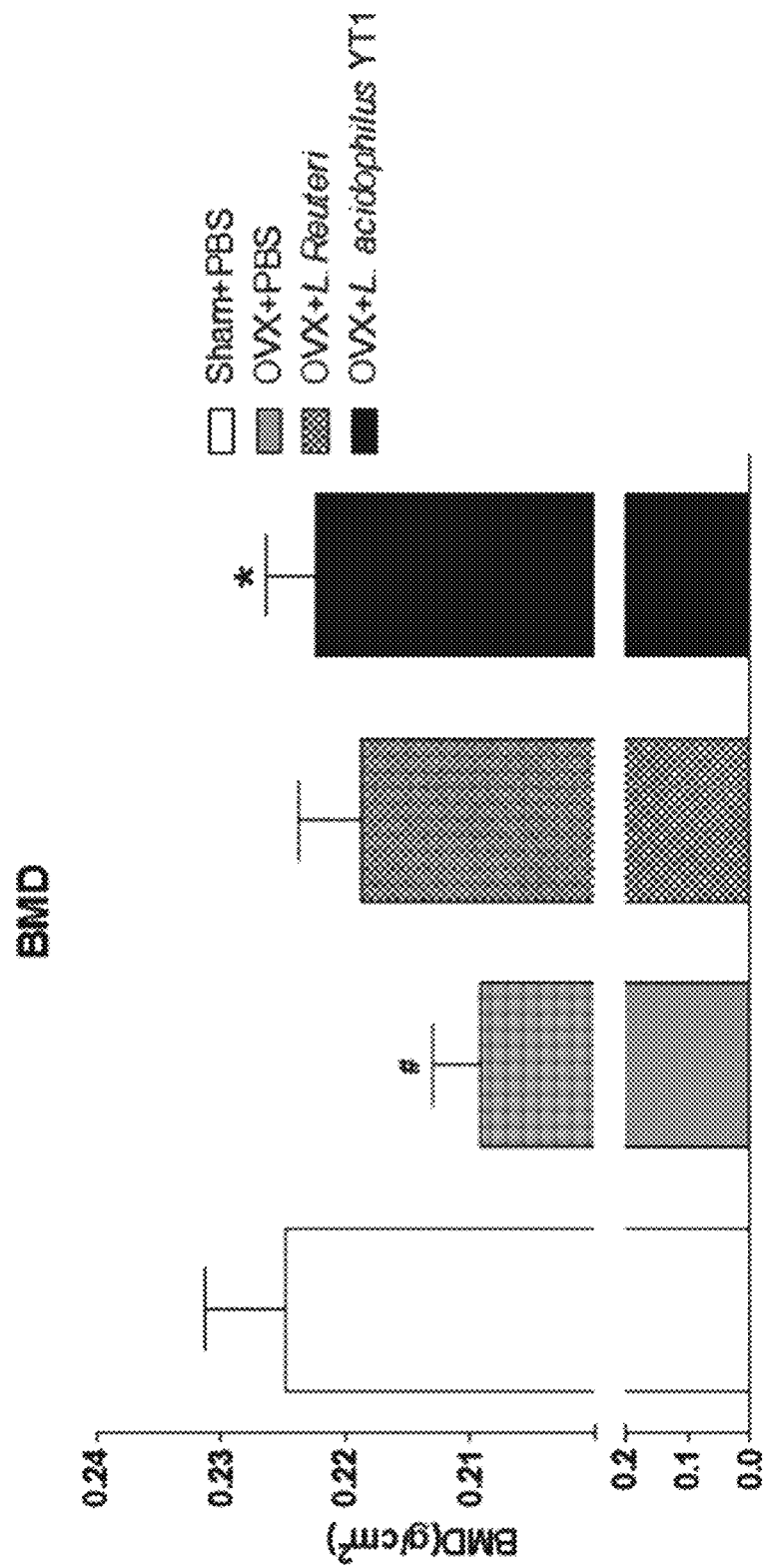
FIGS. 14A and 14B show a femoral bone mineral density (FIG. 14A) and pain sensitivity (FIG. 14B) of rats at week 12 of sample administration after ovariectomy in order to compare efficacies of a *Lactobacillus acidophilus* strain and a strain of a different species of the genus *Lactobacillus*.

As a result, as shown in FIG. 14A, in the ovariectomy group (OVX+PBS), compared with the control (Sham+PBS), the bone mineral density was continuously decreased. On the other hand, it was confirmed that, in the *Lactobacillus acidophilus* YT1-administered group, compared with the ovariectomy group, the bone mineral density was significantly increased, whereas in the *Lactobacillus reuteri*-administered group, compared with the *Lactobacillus acidophilus* YT1-administered group, no statistically significant increase in bone mineral density was shown even though *Lactobacillus reuteri* was administered at a dose 10-fold higher than *Lactobacillus acidophilus*.

6-2. Analysis of Pain Sensitivity

To compare the efficacy of the change in pain sensitivity between the *Lactobacillus acidophilus* strain and the strain of a different species of the genus *Lactobacillus* (*L. reuteri*) in menopausal animal models, after ovariectomy, rats at week 12 of sample administration were subjected to a von Frey filament test according to the method described in Example 1-4 to measure pain sensitivity.

Figure 14B:
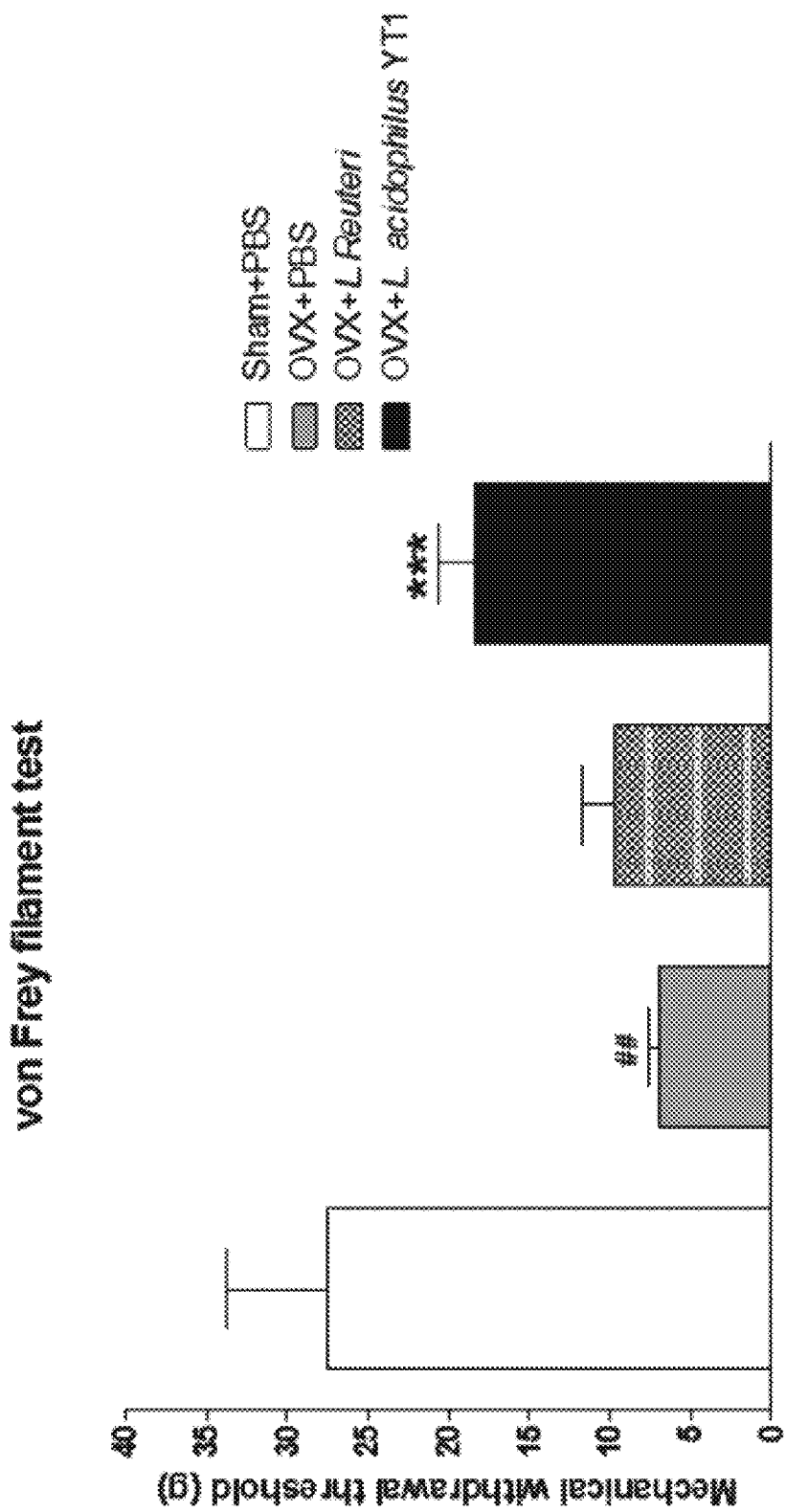

As a result, as shown in FIG. 14B, it was confirmed that, compared with the control (Sham+PBS), in the ovariectomy group (OVX+PBS), the threshold of the force at which pain was felt was significantly decreased, indicating an increase in pain sensitivity. On the other hand, in the *Lactobacillus acidophilus* YT1-administered group, compared with the ovariectomy group, the threshold of the force at which pain was felt was significantly increased, indicating a decrease in pain sensitivity. However, it was confirmed that, in the *Lactobacillus reuteri*-administered group, even though *Lactobacillus reuteri* was administered at a dose 10-fold higher than the *Lactobacillus acidophilus* YT1-administered group, the threshold of the force at which pain was felt did not show a statistically significant increase, compared with the ovariectomy group.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

The inventors have identified and isolated a novel *Lactobacillus acidophilus* strain, and confirmed effects of the novel strain and a previously reported *Lactobacillus acidophilus* strain on alleviation of menopausal symptoms such as the inhibition of an increase in body fat, a decrease in bone mineral density and an increase in pain sensitivity, and the alleviation of depression, etc. Therefore, it is expected that the composition including *Lactobacillus acidophilus* according to the present invention can be effectively used for preventing, alleviating or treating menopause.

The invention claimed is:

1. A method for preventing or treating a menopausal symptom, comprising administering a pharmaceutical composition comprising an effective amount of *Lactobacillus acidophilus* to a subject in need thereof, wherein the menopausal symptom is an increase in body fat, a decrease in bone mineral density, an increase in pain sensitivity, or a depression, wherein the *Lactobacillus acidophilus* is a *Lactobacillus acidophilus* YT1 strain (Deposition Number: KCCM 11808P) or a *Lactobacillus acidophilus* KCTC 3164 strain.

* * * * *